(12) United States Patent
Neufeld et al.

(10) Patent No.: US 9,044,419 B2
(45) Date of Patent: Jun. 2, 2015

(54) VACCINE COMPOSITIONS COMPROMISING βS-CRYSTALLIN FOR INDUCING IMMUNE RESPONSES AGAINST COMPONENTS OF DRUSEN

(75) Inventors: Arthur H. Neufeld, Chicago, IL (US); Ai Ling Wang, Chicago, IL (US)

(73) Assignee: Northwestern University, Evanston, IL (US)

( * ) Notice: Subject to any disclaimer, the term of this patent is extended or adjusted under 35 U.S.C. 154(b) by 176 days.

(21) Appl. No.: 13/188,982

(22) Filed: Jul. 22, 2011

(65) Prior Publication Data

US 2011/0300166 A1 Dec. 8, 2011

Related U.S. Application Data

(63) Continuation of application No. 12/404,990, filed on Mar. 16, 2009, now abandoned.

(60) Provisional application No. 61/037,091, filed on Mar. 17, 2008.

(51) Int. Cl.
*A61K 38/00* (2006.01)
*A61K 39/00* (2006.01)

(52) U.S. Cl.
CPC .................................. *A61K 39/0008* (2013.01)

(58) Field of Classification Search
None
See application file for complete search history.

(56) References Cited

U.S. PATENT DOCUMENTS

| 5,871,739 A | 2/1999 | Inoue |
|---|---|---|
| 2003/0017501 A1 | 1/2003 | Hageman et al. |
| 2006/0121039 A1 | 6/2006 | Sharif |

FOREIGN PATENT DOCUMENTS

WO 2006053903 5/2006

OTHER PUBLICATIONS

De et al., "Human retinal pigment epithelium cell changes and expression of alphaB-crystallin: a biomarker for retinal pigment epithelium cell change in age-related macular degeneration", Arch. Ophthalmol., 2007 125(5):641-645.
Johnson et al., "Drusen-associated degeneration in the retina", Invest. Ophthalmol. Vis. Sci., 2003, 44 (10):4481-4488.
Nakata et al., "Crystallin distribution in Bruch's membrane-choroid complex from AMD and age-matched donor eyes", Experimental Eye Research, 2005, 80:821-826.
Mullins et al., "Drusen associated with aging and age-related macular degeneration contain proteins common to extracellular deposits associated with atherosclerosis, elastosis, amyloidosis and dense deposit disease", Faseb. J., 2000, 14:835-846.
International Search Report for PCT/US2009/037294 dated Nov. 5, 2009.
Written Opinion for PCT/US2009/037294 dated Nov. 5, 2009.
Corrected Version of Written Opinion for PCT/US2009/037294 dated Nov. 5, 2009.

*Primary Examiner* — Yunsoo Kim
(74) *Attorney, Agent, or Firm* — Andrus Intellectual Property Law LLP

(57) ABSTRACT

Disclosed are compositions and methods for treating or preventing the formation of drusen in a patient in need thereof. The compositions include an effective amount of at least one polypeptide present in drusen, or an immunogenic fragment or variant thereof that induces an immune response against the polypeptide, together with a pharmaceutical carrier, excipient, or diluent. The compositions are suitable as vaccines for treating or preventing drusen and diseases associated with drusen.

12 Claims, 13 Drawing Sheets

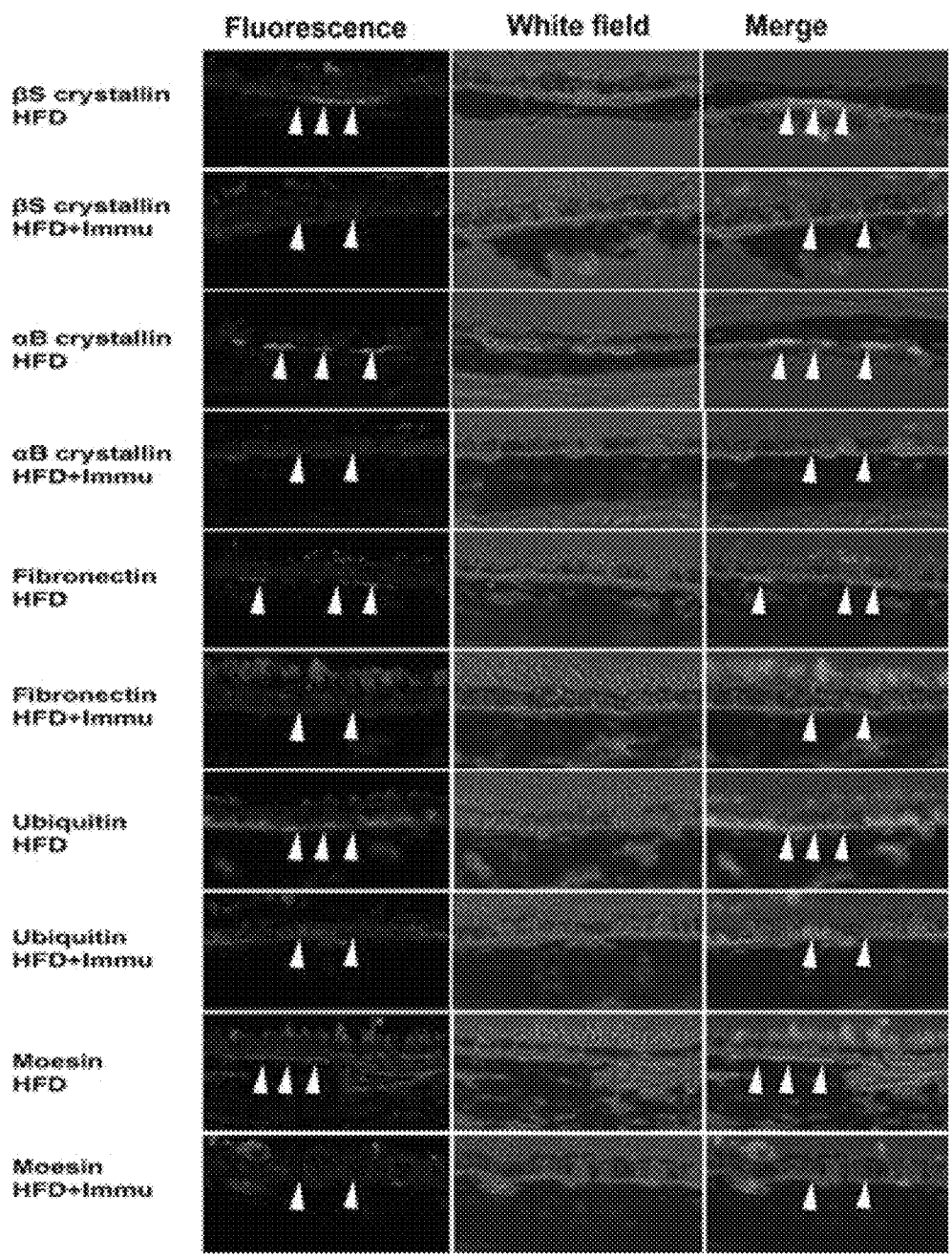

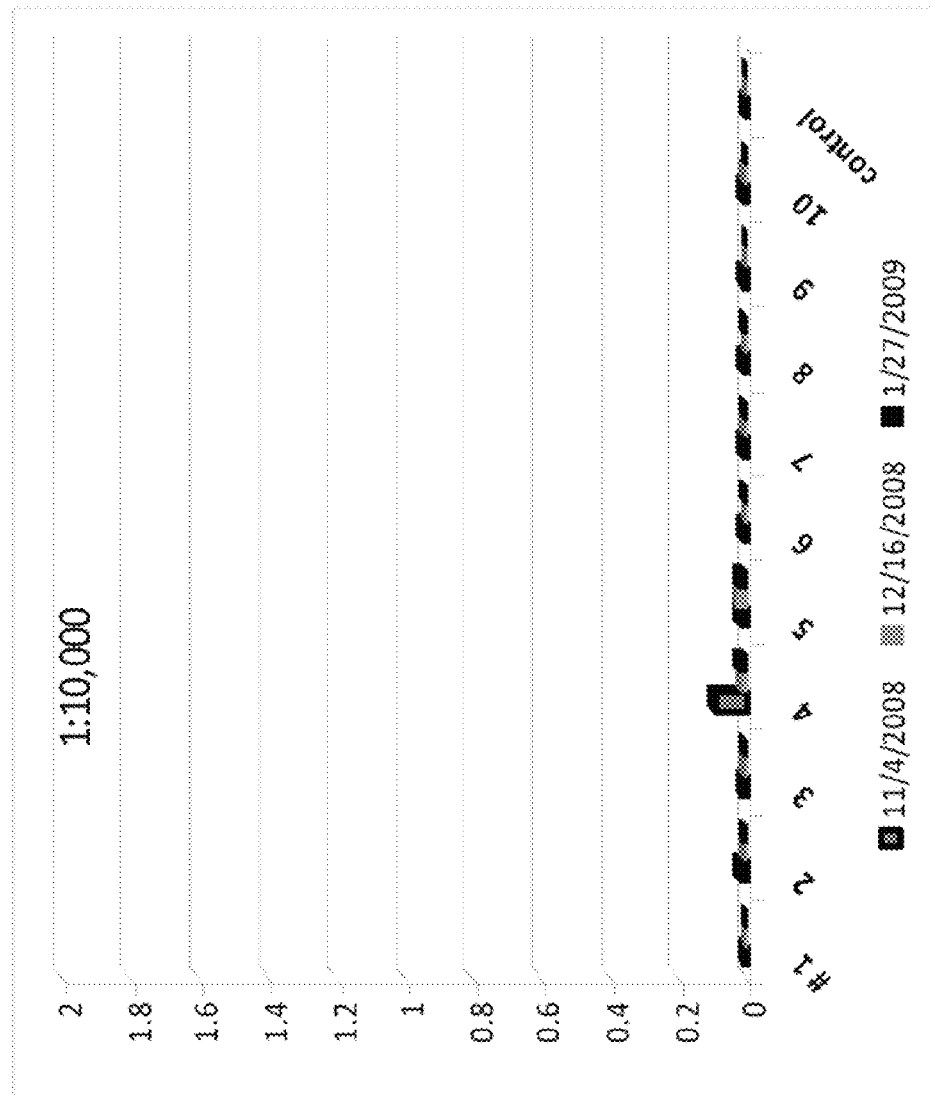

Figure 1:
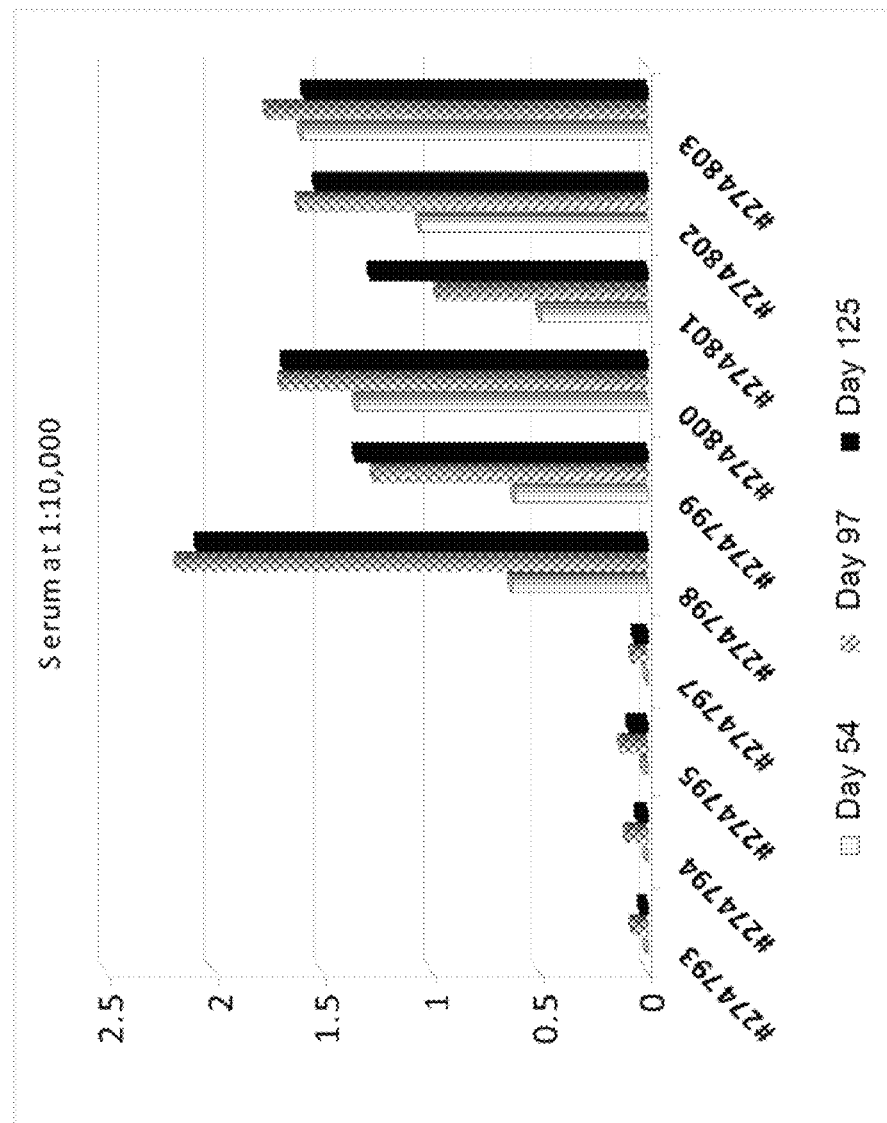

1~5: Control
6~10: CD63 immu

SEQUENCE LISTING

```
<160> NUMBER OF SEQ ID NOS: 10

<210> SEQ ID NO 1
<211> LENGTH: 178
<212> TYPE: PRT
<213> ORGANISM: Homo Sapiens
<220> FEATURE:
<221> NAME/KEY: Polypeptide
<222> LOCATION: (1)..(178)

<400> SEQUENCE: 1

Met Ser Lys Thr Gly Thr Lys Ile Thr Phe Tyr Glu Asp Lys Asn Phe
1               5                   10                  15

Gln Gly Arg Arg Tyr Asp Cys Asp Cys Asp Cys Ala Asp Phe His Thr
            20                  25                  30

Tyr Leu Ser Arg Cys Asn Ser Ile Lys Val Glu Gly Gly Thr Trp Ala
        35                  40                  45

Val Tyr Glu Arg Pro Asn Phe Ala Gly Tyr Met Tyr Ile Leu Pro Gln
    50                  55                  60

Gly Glu Tyr Pro Glu Tyr Gln Arg Trp Met Gly Leu Asn Asp Arg Leu
65                  70                  75                  80

Ser Ser Cys Arg Ala Val His Leu Pro Ser Gly Gly Gln Tyr Lys Ile
                85                  90                  95

Gln Ile Phe Glu Lys Gly Asp Phe Ser Gly Gln Met Tyr Glu Thr Thr
            100                 105                 110

Glu Asp Cys Pro Ser Ile Met Glu Gln Phe His Met Arg Glu Ile His
        115                 120                 125
```

```
Ser Cys Lys Val Leu Glu Gly Val Trp Ile Phe Tyr Glu Leu Pro Asn
130                 135                 140

Tyr Arg Gly Arg Gln Tyr Leu Leu Asp Lys Lys Glu Tyr Arg Lys Pro
145                 150                 155                 160

Ile Asp Trp Gly Ala Ala Ser Pro Ala Val Gln Ser Phe Arg Arg Ile
                165                 170                 175

Val Glu

<210> SEQ ID NO 2
<211> LENGTH: 175
<212> TYPE: PRT
<213> ORGANISM: Homo Sapiens
<220> FEATURE:
<221> NAME/KEY: Polypeptide
<222> LOCATION: (1)..(175)

<400> SEQUENCE: 2

Met Asp Ile Ala Ile His His Pro Trp Ile Arg Arg Pro Phe Phe Pro
1               5                   10                  15

Phe His Ser Pro Ser Arg Leu Phe Asp Gln Phe Phe Gly Glu His Leu
                20                  25                  30

Leu Glu Ser Asp Leu Phe Pro Thr Ser Thr Ser Leu Ser Pro Phe Tyr
            35                  40                  45

Leu Arg Pro Pro Ser Phe Leu Arg Ala Pro Ser Trp Phe Asp Thr Gly
50                  55                  60

Leu Ser Glu Met Arg Leu Glu Lys Asp Arg Phe Ser Val Asn Leu Asp
65                  70                  75                  80

Val Lys His Phe Ser Pro Glu Glu Leu Lys Val Lys Val Leu Gly Asp
                85                  90                  95

Val Ile Glu Val His Gly Lys His Glu Glu Arg Gln Asp Glu His Gly
            100                 105                 110

Phe Ile Ser Arg Glu Phe His Arg Lys Tyr Arg Ile Pro Ala Asp Val
        115                 120                 125

Asp Pro Leu Thr Ile Thr Ser Ser Leu Ser Ser Asp Gly Val Leu Thr
130                 135                 140

Val Asn Gly Pro Arg Lys Gln Val Ser Gly Pro Glu Arg Thr Ile Pro
145                 150                 155                 160

Ile Thr Arg Glu Glu Lys Pro Ala Val Thr Ala Ala Pro Lys Lys
                165                 170                 175

<210> SEQ ID NO 3
<211> LENGTH: 466
<212> TYPE: PRT
<213> ORGANISM: Homo Sapiens
<220> FEATURE:
<221> NAME/KEY: Polypeptide
<222> LOCATION: (1)..(466)

<400> SEQUENCE: 3

Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
                20                  25                  30

Thr Ser Thr Arg Thr Tyr Ser Leu Gly Ser Ala Leu Arg Pro Ser Thr
            35                  40                  45

Ser Arg Ser Leu Tyr Ala Ser Ser Pro Gly Gly Val Tyr Ala Thr Arg
50                  55                  60
```

```
Ser Ser Ala Val Arg Leu Arg Ser Ser Val Pro Gly Val Arg Leu Leu
 65                  70                  75                  80

Gln Asp Ser Val Asp Phe Ser Leu Ala Asp Ala Ile Asn Thr Glu Phe
                 85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
            115                 120                 125

Lys Ile Leu Leu Ala Glu Leu Glu Gln Leu Lys Gly Gln Gly Lys Ser
130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
            195                 200                 205

Asp Val Asp Asn Ala Ser Leu Ala Arg Leu Asp Leu Glu Arg Lys Val
210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
            275                 280                 285

Glu Trp Tyr Lys Ser Lys Phe Ala Asp Leu Ser Glu Ala Ala Asn Arg
            290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
            355                 360                 365

Ile Gln Asn Met Lys Glu Glu Met Ala Arg His Leu Arg Glu Tyr Gln
370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
            450                 455                 460

Leu Glu
465
```

```
<210> SEQ ID NO 4
<211> LENGTH: 417
<212> TYPE: PRT
<213> ORGANISM: Homo Sapiens
<220> FEATURE:
<221> NAME/KEY: Polypeptide
<222> LOCATION: (1)..(417)

<400> SEQUENCE: 4
```

Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
                20                  25                  30

Trp Thr Ser Arg Trp Ile Glu Ser Lys His Lys Ser Asp Phe Gly Lys
            35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
                100                 105                 110

Phe Pro Asn Ser Leu Asp Gln Thr Asp Met His Gly Asp Ser Glu Tyr
            115                 120                 125

Asn Ile Met Phe Gly Pro Asp Ile Cys Gly Pro Gly Thr Lys Lys Val
            130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
    290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

```
Glu Glu Glu Glu Asp Lys Lys Arg Lys Glu Glu Glu Ala Glu Asp
            370             375             380

Lys Glu Asp Asp Glu Asp Lys Asp Glu Asp Glu Asp Glu Glu Asp
385             390             395             400

Lys Glu Glu Asp Glu Glu Glu Asp Val Pro Gly Gln Ala Lys Asp Glu
                405             410             415

Leu

<210> SEQ ID NO 5
<211> LENGTH: 165
<212> TYPE: PRT
<213> ORGANISM: Homo Sapiens
<220> FEATURE:
<221> NAME/KEY: Polypeptide
<222> LOCATION: (1)..(165)

<400> SEQUENCE: 5

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu
                165

<210> SEQ ID NO 6
<211> LENGTH: 130
<212> TYPE: PRT
<213> ORGANISM: Homo Sapiens
<220> FEATURE:
<221> NAME/KEY: Polypeptide
<222> LOCATION: (1)..(130)

<400> SEQUENCE: 6

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ser Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
```

```
                65                  70                  75                  80
Pro Arg His Leu Gln Leu Ala Ile Arg Asn Asp Glu Glu Leu Asn Lys
                    85                  90                  95

Leu Leu Gly Arg Val Thr Ile Ala Gln Gly Gly Val Leu Pro Asn Ile
                100                 105                 110

Gln Ala Val Leu Leu Pro Lys Lys Thr Glu Ser His His Lys Ala Lys
                115                 120                 125

Gly Lys
    130

<210> SEQ ID NO 7
<211> LENGTH: 130
<212> TYPE: PRT
<213> ORGANISM: Homo Sapiens
<220> FEATURE:
<221> NAME/KEY: Polypeptide
<222> LOCATION: (1)..(130)

<400> SEQUENCE: 7

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
                20                  25                  30

Arg Leu Leu Arg Lys Gly Asn Tyr Ala Glu Arg Val Gly Ala Gly Ala
                35                  40                  45

Pro Val Tyr Leu Ala Ala Val Leu Glu Tyr Leu Thr Ala Glu Ile Leu
            50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                    85                  90                  95

Leu Leu Gly Lys Val Thr Ile Ala Gln Gly Gly Val Leu Pro Asn Ile
                100                 105                 110

Gln Ala Val Leu Leu Pro Lys Lys Thr Glu Ser His His Lys Ala Lys
                115                 120                 125

Gly Lys
    130

<210> SEQ ID NO 8
<211> LENGTH: 128
<212> TYPE: PRT
<213> ORGANISM: Homo Sapiens
<220> FEATURE:
<221> NAME/KEY: Polypeptide
<222> LOCATION: (1)..(128)

<400> SEQUENCE: 8

Met Ala Gly Gly Lys Ala Gly Lys Asp Ser Gly Lys Ala Lys Thr Lys
1               5                   10                  15

Ala Val Ser Arg Ser Gln Arg Ala Gly Leu Gln Phe Pro Val Gly Arg
                20                  25                  30

Ile His Arg His Leu Lys Ser Arg Thr Thr Ser His Gly Arg Val Gly
                35                  40                  45

Ala Thr Ala Ala Val Tyr Ser Ala Ala Ile Leu Glu Tyr Leu Thr Ala
            50                  55                  60

Glu Val Leu Glu Leu Ala Gly Asn Ala Ser Lys Asp Leu Lys Val Lys
65                  70                  75                  80

Arg Ile Thr Pro Arg His Leu Gln Leu Ala Ile Arg Gly Asp Glu Glu
```

```
                    85                  90                  95

Leu Asp Ser Leu Ile Lys Ala Thr Ile Ala Gly Gly Val Ile Pro
            100                 105                 110

His Ile His Lys Ser Leu Ile Gly Lys Gly Gln Gln Lys Thr Val
            115                 120                 125

<210> SEQ ID NO 9
<211> LENGTH: 126
<212> TYPE: PRT
<213> ORGANISM: Homo Sapiens
<220> FEATURE:
<221> NAME/KEY: Polypeptide
<222> LOCATION: (1)..(126)

<400> SEQUENCE: 9

Met Pro Glu Pro Ser Lys Ser Ala Pro Ala Pro Lys Lys Gly Ser Lys
1               5                   10                  15

Lys Ala Ile Thr Lys Ala Gln Lys Lys Asp Gly Lys Lys Arg Lys Arg
            20                  25                  30

Ser Arg Lys Glu Ser Tyr Ser Ile Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125

<210> SEQ ID NO 10
<211> LENGTH: 239
<212> TYPE: PRT
<213> ORGANISM: Homo Sapiens
<220> FEATURE:
<221> NAME/KEY: Polypeptide
<222> LOCATION: (1)..(239)

<400> SEQUENCE: 10

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
```

-continued

|  | 130 |  |  | 135 |  |  |  | 140 |  |  |  |
|---|---|---|---|---|---|---|---|---|---|---|---|
| Cys 145 | Cys | Gly | Ala | Ala | Asn 150 | Tyr | Thr | Asp | Trp | Glu 155 | Lys Ile Pro Ser Met 160 |
| Ser | Lys | Asn | Arg | Val 165 | Pro | Asp | Ser | Cys | Cys 170 | Ile | Asn Val Thr Val Gly 175 |
| Cys | Gly | Ile | Asn 180 | Phe | Asn | Glu | Lys | Ala 185 | Ile | His | Lys Glu Gly Cys Val 190 |
| Glu | Lys | Ile 195 | Gly | Gly | Trp | Leu | Arg 200 | Lys | Asn | Val | Leu Val Val Ala Ala 205 |
| Ala | Ala | Leu 210 | Gly | Ile | Ala | Phe 215 | Val | Glu | Val | Leu | Gly Ile Val Phe Ala 220 |
| Cys 225 | Cys | Leu | Val | Lys | Ser 230 | Ile | Arg | Ser | Gly | Tyr 235 | Glu Val Met Leu |

VACCINE COMPOSITIONS COMPROMISING βS-CRYSTALLIN FOR INDUCING IMMUNE RESPONSES AGAINST COMPONENTS OF DRUSEN

CROSS-REFERENCE TO RELATED APPLICATION

This application is a continuation of U.S. application Ser. No. 12/404,990, filed oxo Mar. 16, 2009, which application was published on Sep. 17, 2009, as US2009/0232836, and claims the benefit under 35 U.S.C. §119(e) to U.S. Provisional Application No. 61/037,091, filed on Mar. 17, 2008, the entire contents of which are incorporated herein by reference in their entireties.

STATEMENT REGARDING U.S. GOVERNMENT SPONSORED RESEARCH

This invention was made with government support under grant number EY012017 awarded by the National Institutes of Health. The government has certain rights in the invention.

BACKGROUND

The field of the invention relates to methods for treating or preventing macular degeneration. In particular, the invention relates to compositions and methods that are useful for preventing the formation of drusen associated with macular degeneration, such as macular drusen. The compositions and methods also are useful for preventing an increase in the size or amount of existing drusen, or for causing a decrease in the size or amount of existing drusen. The compositions and methods also are useful for preventing the appearance of new drusen.

Macular degeneration is a medical condition predominantly found in elderly adults in which the center of the retina of the eye, otherwise known as the "macula" area of the retina, exhibits thinning, atrophy, and sometimes new blood vessel formation. Macular degeneration can result in the loss of central vision, including the ability to see fine details, to read, or even to recognize faces. According to the American Academy of Ophthalmology, macular degeneration is the leading cause of central vision loss in the United States for those over the age of fifty years. Although macular degeneration sometimes may affect younger individuals, the term generally refers to "age-related" macular degeneration (i.e., "AMD" or "ARMD").

Early stages of AMD are characterized by development of yellow deposits in the macula called drusen. These deposits form in the macula between the retinal pigment epithelium and the underlying choroid. At this early stage (referred to as the maculopathy stage), most patients still have good vision. However, patients with macular drusen can go on to develop advanced AMD. The risk for developing advanced AMD is considerably higher when the drusen are large and numerous or when the drusen are associated with a disturbance in the pigmented cell layer tinder the macula.

Advanced AMD has two forms referred to as the "dry" and "Wet" forms. The dry form of advanced AMD is characterized by central geographic atrophy, which causes vision loss through the loss of photoreceptors in the central part of the eye (i.e., rods and cones). While no treatment is available for the dry form, the National Eye Institute has suggested that vitamin supplements with high doses of antioxidants may slow the progression of dry macular degeneration and in some patients, improve visual acuity.

The wet form of advanced AMD, otherwise referred to as "neovascular" or "exudative" AMD, causes vision loss due to abnormal blood vessel growth in the choriocapillaries, through a retinal layer referred to as "Bruch's membrane." The wet form of AMD ultimately leads to blood and protein leakage below the macula. This bleeding, leaking, and scarring below the macula eventually cause irreversible damage to the photoreceptors and rapid vision loss if left untreated. Until recently, no effective treatments were known for wet macular degeneration. However, new drugs that inhibit angiogenesis (i.e., "anti-angiogenic agents") have been shown to cause regression of the abnormal blood vessels and improvement of vision. In order to be effective, anti-angiogenic agents, such as anti-vascular endothelial growth factor, must be injected directly into the vitreous humor of the eye. Furthermore, anti-angiogenic agents are expensive and must be administered repeatedly several times a year.

Therefore, new compositions and methods for treating or preventing macular degeneration are desirable.

SUMMARY

Disclosed are compositions and methods for treating or preventing the formation of drusen in a patient, which may include macular drusen. The disclosed compositions and methods also may be utilized for treating or preventing diseases associated with drusen. The compositions may be immunogenic and may be useful for preventing formation of drusen, for preventing an increase in size of existing drusen or appearance of new drusen, or for causing a decrease in size or amount of drusen in a patient, thereby treating or preventing diseases associated with macular drusen such as macular degeneration.

The disclosed compositions may include pharmaceutical compositions that are useful as vaccines for treating or preventing drusen formation in a patient. The compositions may include: (a) an effective amount of at least one polypeptide present in drusen or an immunogenic fragment or variant of the polypeptide for inducing or eliciting an immune response against the polypeptide: and (b) a pharmaceutical carrier, excipient, or diluent. In some embodiments; the polypeptide may be selected from a group consisting of: $\beta_s$-crystallin: α-B-crystallin; vimentin; calreticulin or calreticulin precursor; and cyclophilin A (i.e., peptidylprolyl isomerase A). Optionally, the compositions may include a pharmaceutically acceptable adjuvant (e.g., an immunological adjuvant).

After the composition is administered to the patient, the composition is effective at inducing or eliciting an immune response, such as an antibody-mediated immune response or a cell-mediated immune response against at least one component present in drusen (e.g., a polypeptide). In some embodiments, the composition may comprise an immunogen that is a polypeptide present in drusen or that induces or elicits an immune response against a polypeptide that is present in drusen. After the composition is administered to a patient, the resulting immune response is effective for treating drusen or preventing the formation of drusen in the patient. In some embodiments, the administered composition is effective for inhibiting formation of drusen in the patient. In other embodiments, the administered composition is effective for reducing existing drusen in the patient or for slowing or preventing further enlargement of existing drusen in the patient. In further embodiments, the administered composition is effective for preventing formation of drusen in the patient. The administered composition further may treat or prevent macular degeneration in a patient having macular degeneration or at risk for developing macular degeneration.

In some embodiments, the composition may include an effective amount of at least one polypeptide present in drusen or an immunogenic fragment or variant of the polypeptide that is effective for inducing or eliciting an immune response against the polypeptide. For example, the composition may include an effective amount of at least one polypeptide that normally is present intracellularly but is present extracellularly in drusen. Suitable polypeptides may include, but are not limited to a polypeptide selected from a group consisting of: $\beta_s$-crystallin; α-B-crystallin; vimentin; calreticulin precursor; cyclophilin A (i.e., peptidylprolyl isomerase A); or an immunogenic fragment or variant of these polypeptides that is effective for inducing or eliciting an immune response against these polypeptides. In further embodiments, the composition may include an additional polypeptide present in drusen other than $\beta_s$-crystallin; α-B-crystallin; vimentin; calreticulin precursor; cyclophilin A (i.e., peptidylprolyl isomerase A); or an immunogenic fragment or variant of the additional polypeptide that is effective for inducing or eliciting an immune response against this additional polypeptide. For example, the composition further may include another drusen protein as discussed herein or as known in the art.

The disclosed compositions may be immunogenic compositions and may be useful as vaccines. In some embodiments, the compositions may be administered to a patient, where after the composition is administered to the patient, the patient produces antibodies against one or more components of drusen. In further embodiments, after the composition is administered to the patient, the patient exhibits a T-cell response against one or more components of drusen. In even further embodiments, after the composition is administered to the patient, the patient produces antibodies against one or more components of drusen and exhibits a T-cell response against one or more components of drusen.

The disclosed compositions may be effective for treating or preventing drusen and diseases associated with drusen. In some embodiments, the compositions may be effective for treating or preventing macular degeneration (e.g., the dry form, wet form, or both forms of age-related macular degeneration (AMD)).

Also disclosed are methods for treating or preventing the formation of drusen in a patient and diseases associated with the formation of drusen in a patient (e.g., macular degeneration, such as the dry or wet forms of age-related macular degeneration). The methods may include administering any of the compositions disclosed herein to a patient in need thereof (e.g., a patient exhibiting drusen or at risk for developing drusen and diseases associated with macular drusen such as macular degeneration).

Also disclosed are kits. The disclosed kits may include components for preparing the compositions described herein (e.g., lyophilized polypeptides and solvents for resuspending or dissolving the lyophilized polypeptides). The disclosed kits also may include components for administering the compositions described herein to a patient in need thereof.

BRIEF DISCUSSION OF THE FIGURES

FIG. 1. Illustrates the anti-$\beta_s$-crystallin antibody titers in control mice (#'s 793, 794, 795, and 797) and mice immunized with $\beta_s$-crystallin (#'s 798, 799, 800, 801, 802, and 803).

Figure 2:
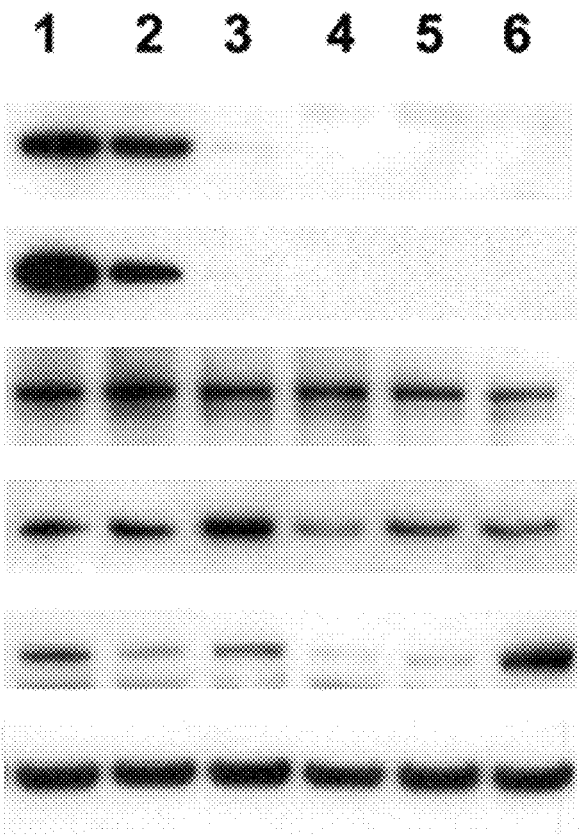

FIG. 2. Western Blot analysis of drusen components in the RPE/choroid from control mice (lanes 1 and 2) and from mice immunized with $\beta_s$-crystallin (lanes 3-6).

Figure 3:
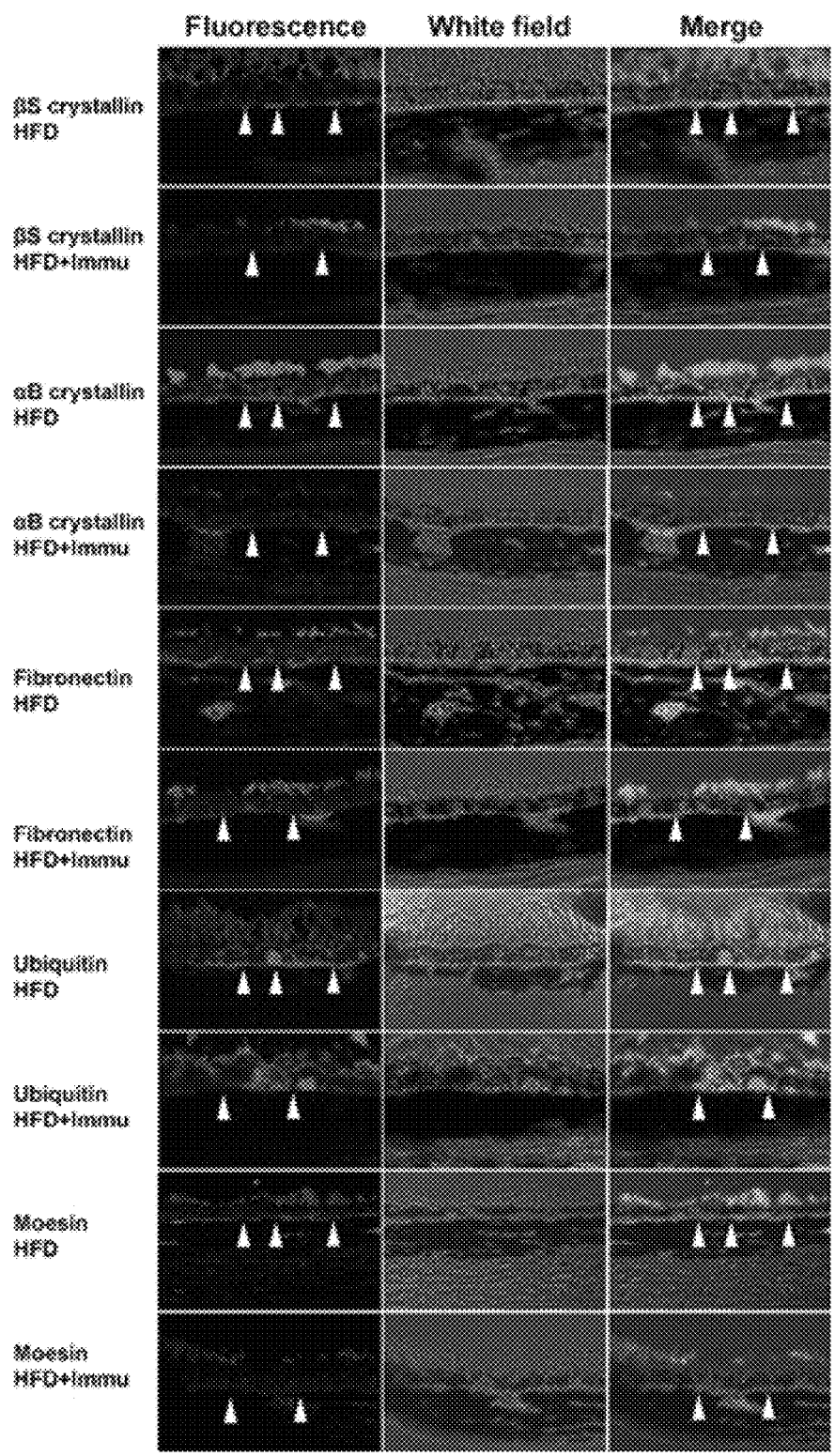
Figure 4A:
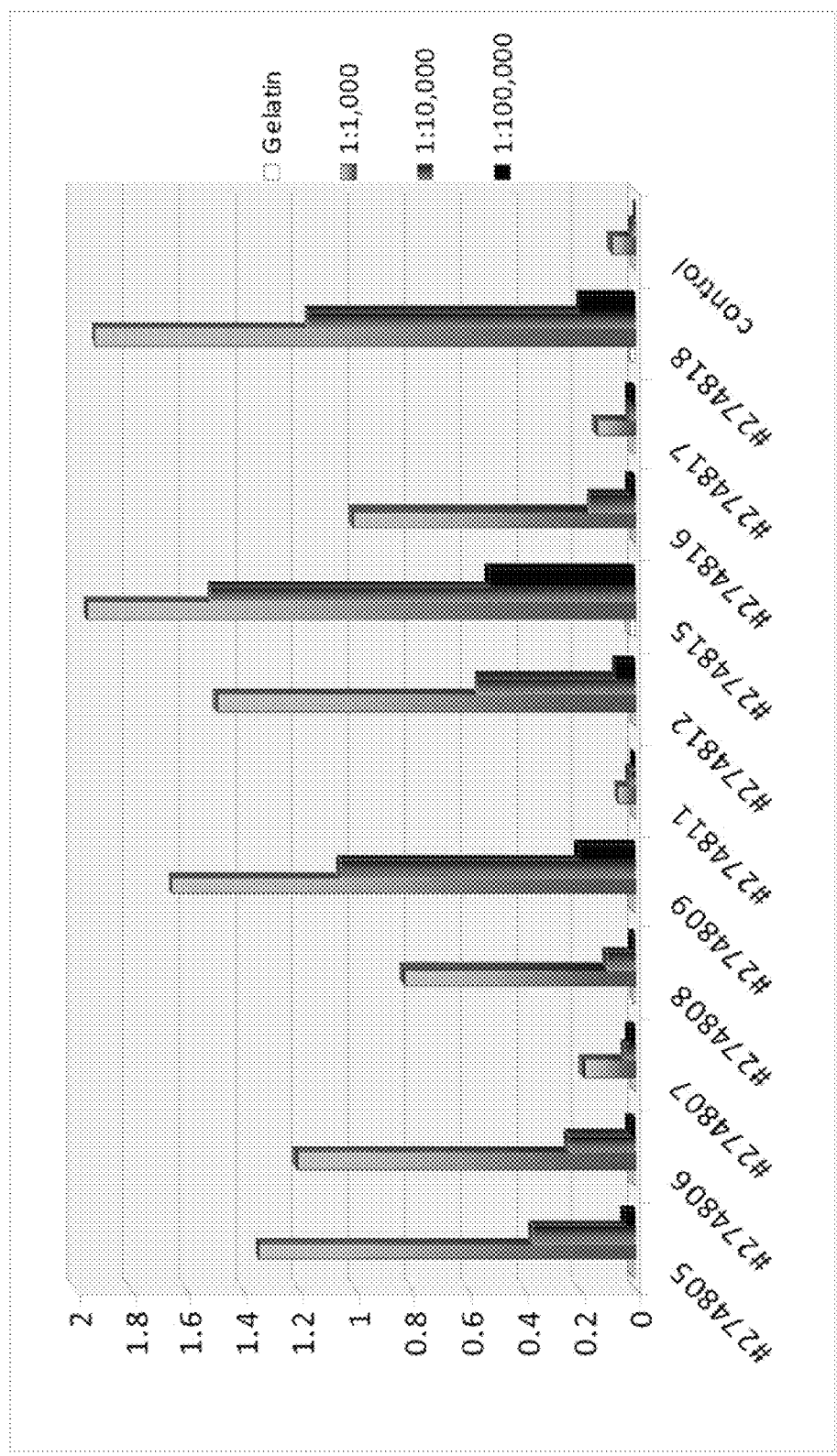
Figure 4B:
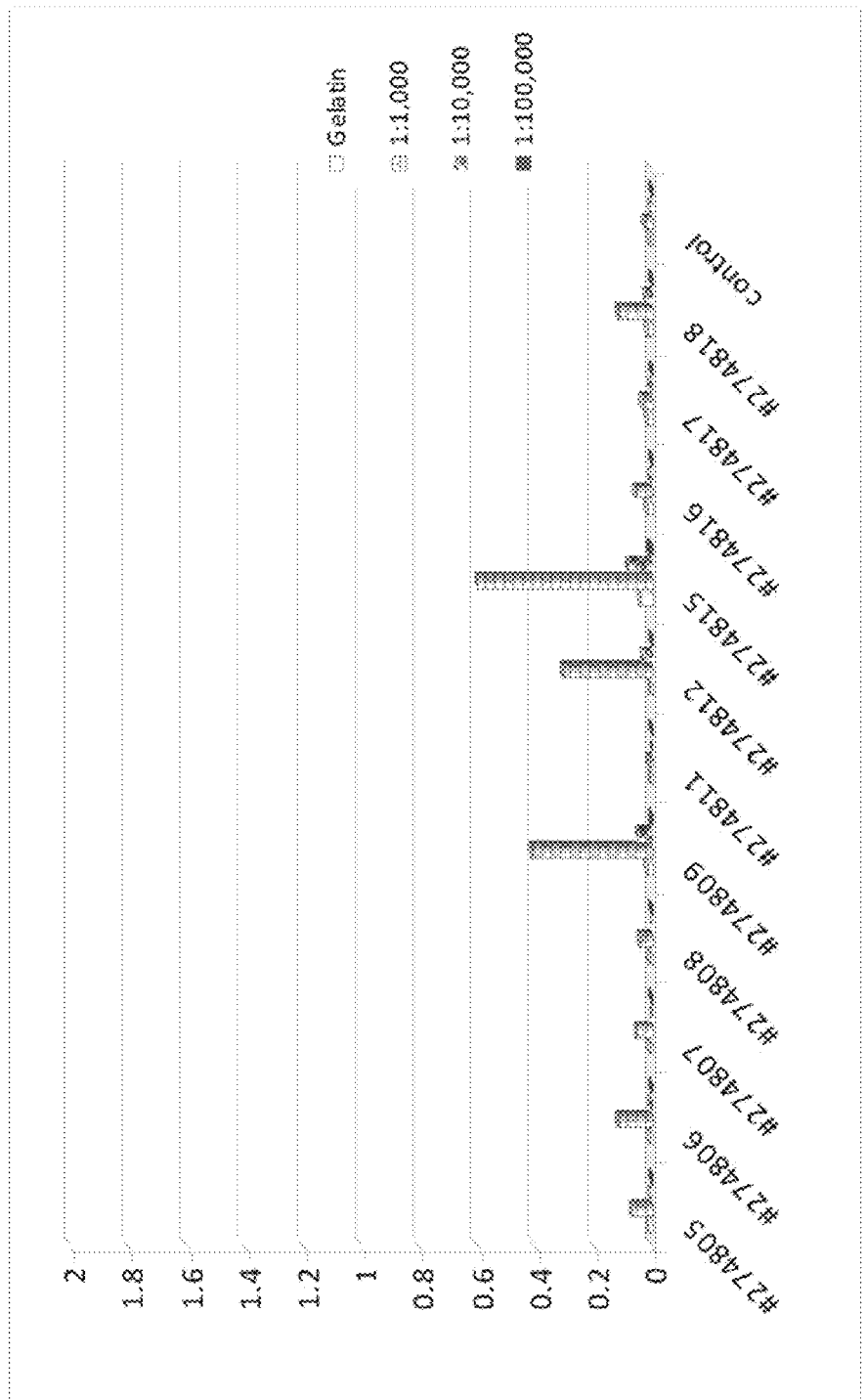
Figure 4C:
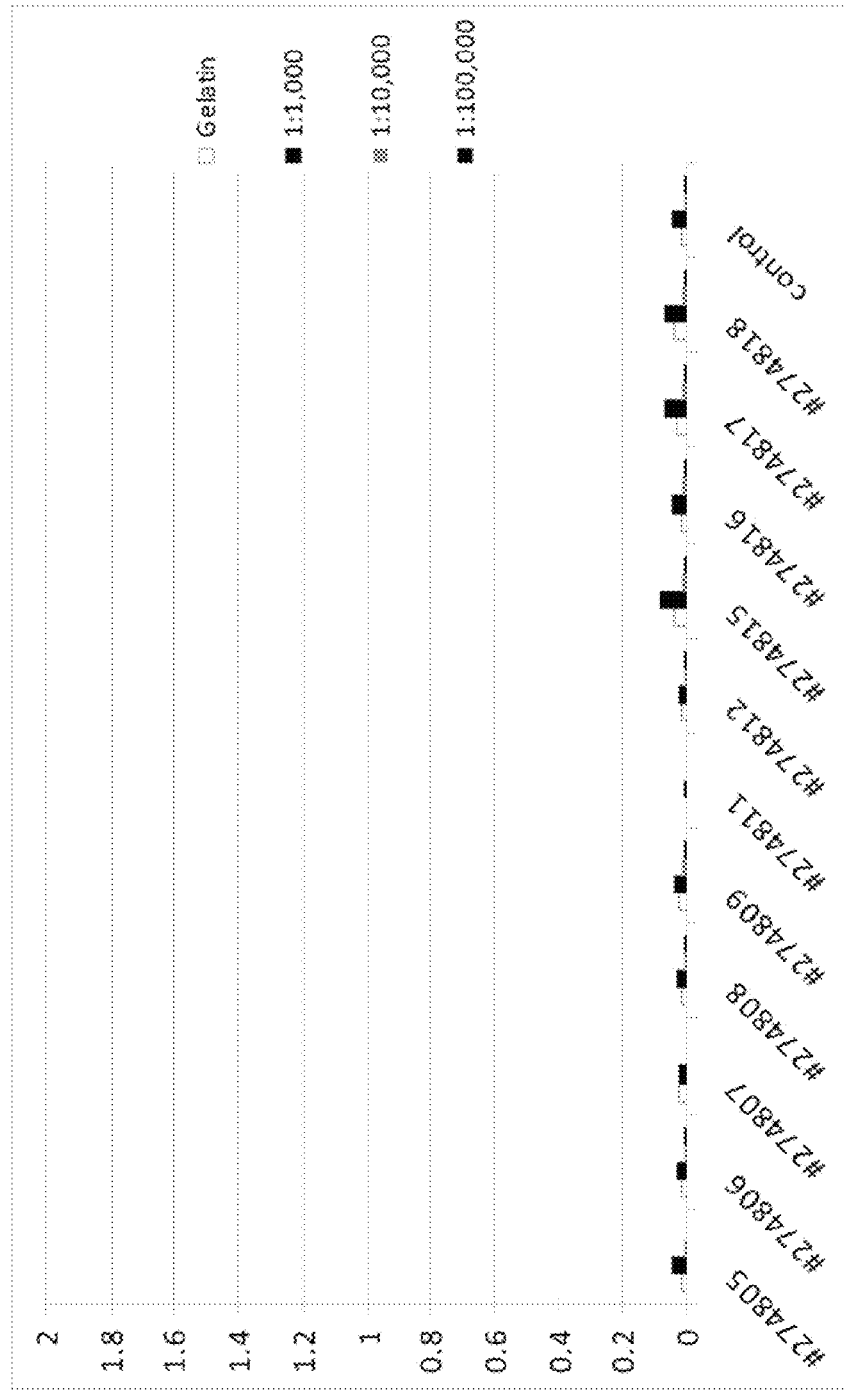
Figure 4D:
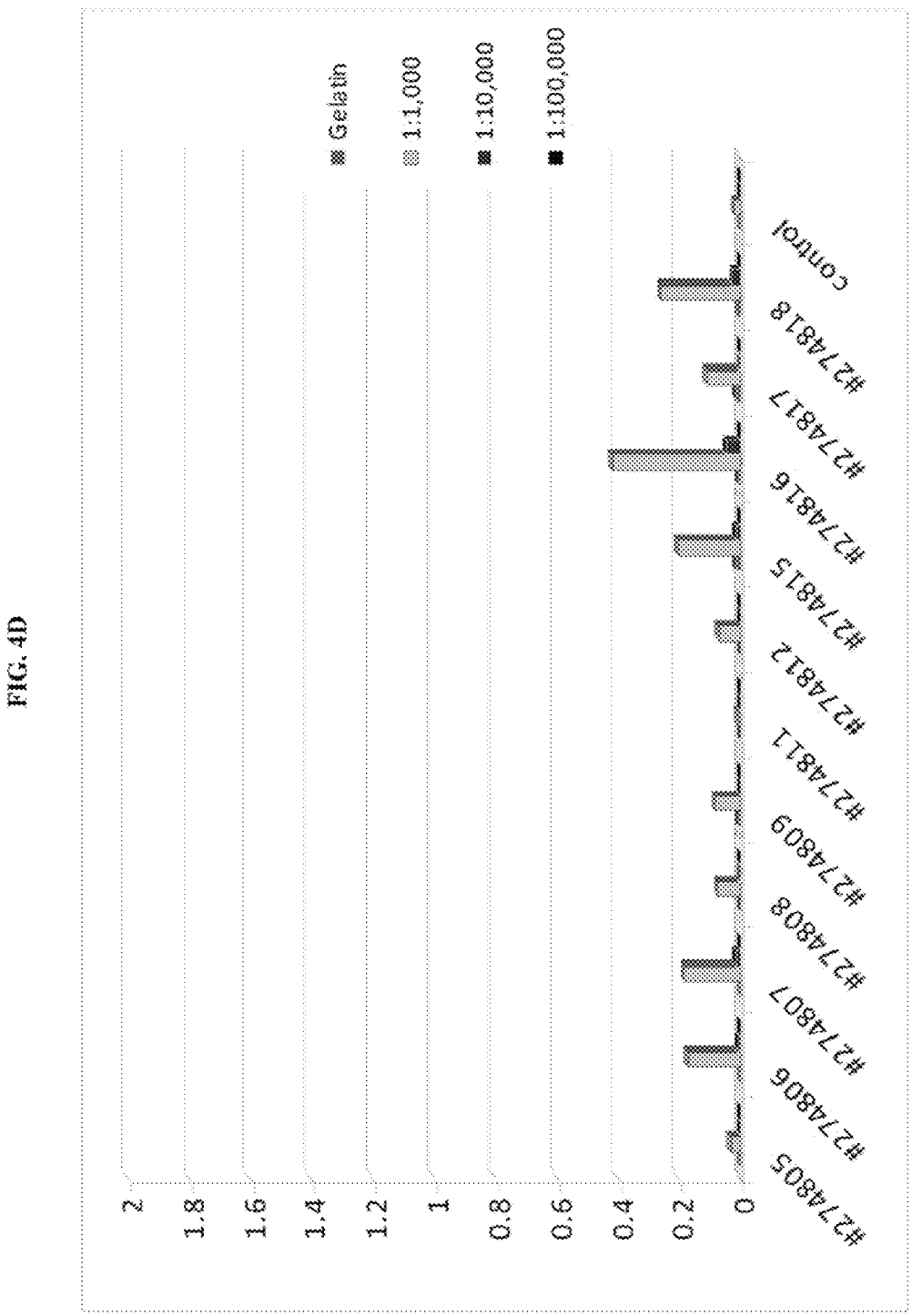
Figure 4E:
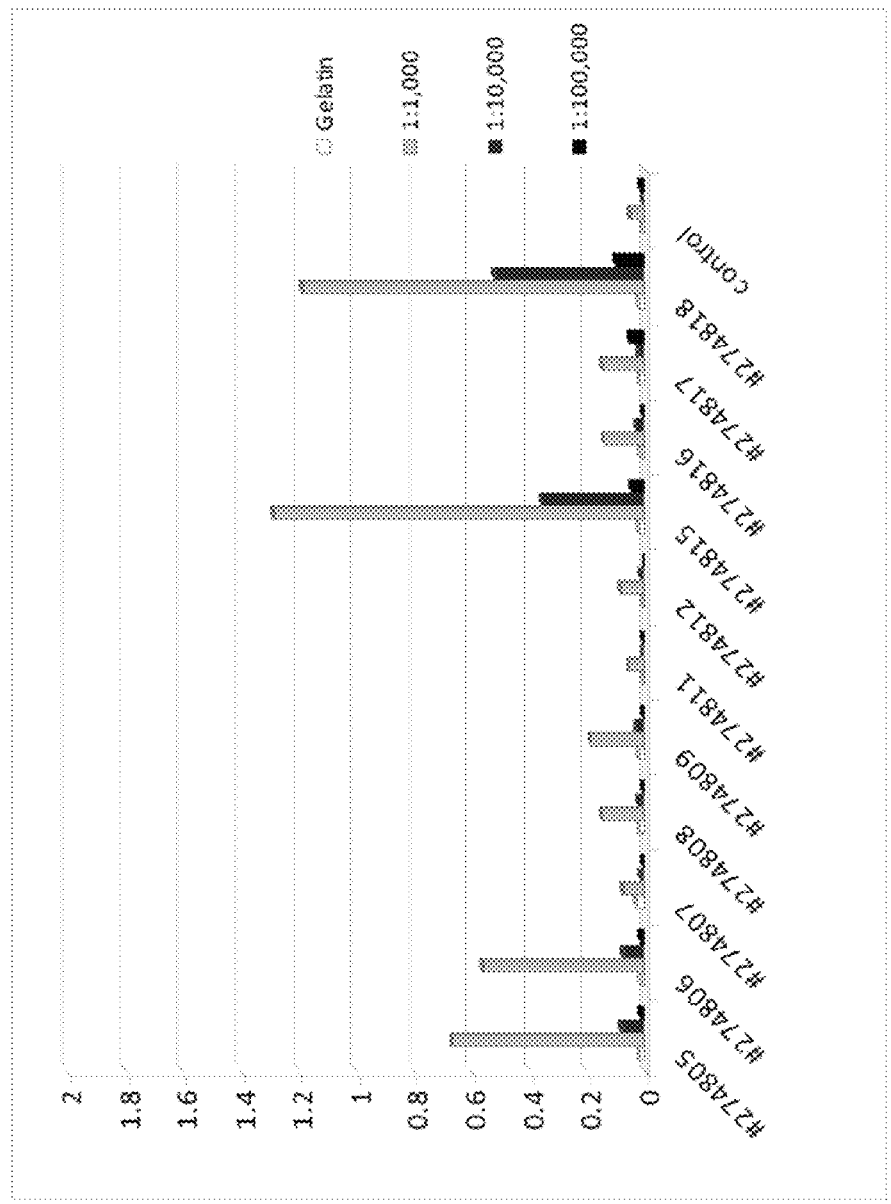

FIG. 3. Immunohistochemistry of enucleated eyes from control mice and mice immunized with $\beta_s$-crystallin.

FIG. 4. Illustrates the antibody titers in control mice (#'s 807, 811, and 817) and immunized mice (#'s 805, 806, 808, 809, 812, 815, 816, and 818). A. Anti-$\beta_s$-crystallin antibody titers; B. Anti-αB crystallin antibody titers; C. Anti-cyclophilin A antibody titers; D. Anti-vimentin antibody titers; and E. Anti-calreticulin antibody titers.

Figure 5:
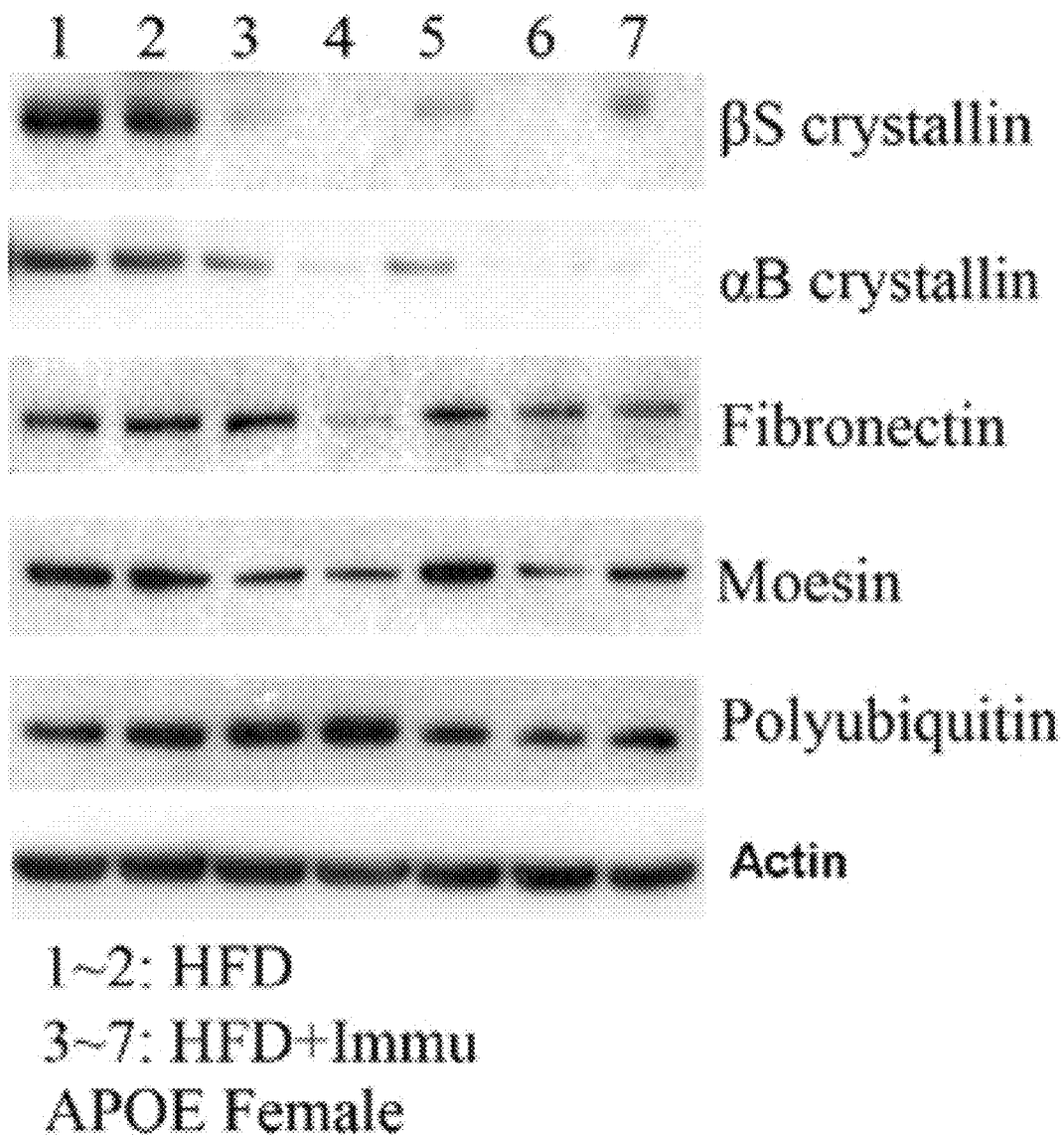

FIG. 5. Western Blot analysis of drusen components in the RPE/choroid from control mice (lanes 1 and 2) and from mice immunized with mixture of $\beta_s$-crystallin, αB crystallin, cyclophilin A, vimentin, and calreticulin (lanes 3-7).

FIG. 6. Immunohistochemistry of enucleated eyes from control mice and mice immunized with mixture of $\beta_s$-crystallin, αB crystallin, cyclophilin A, vimentin, and calreticulin.

Figure 7B:
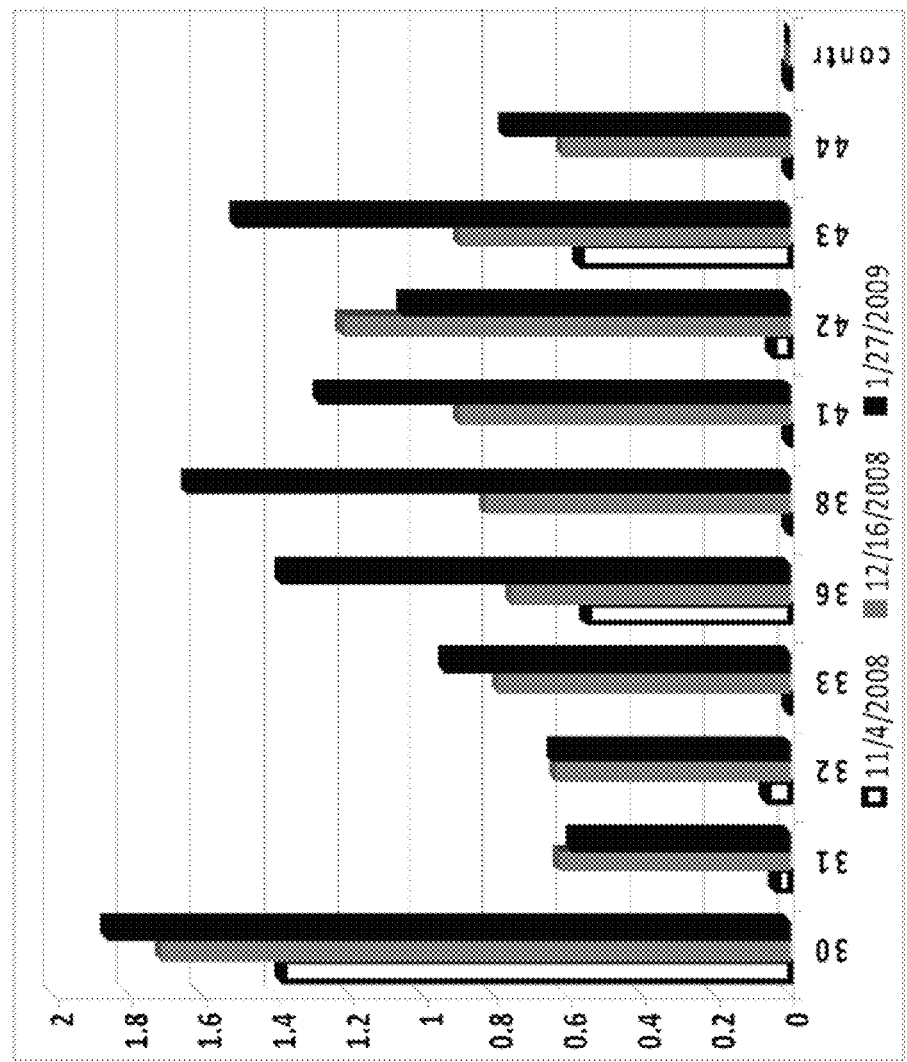

FIG. 7. Illustrates the anti-CD63 antibody titers in control mice (#'s 1-10) and mice immunized with CD63 (#'s 30-33, 36, 38, and 41-44).

Figure 8:
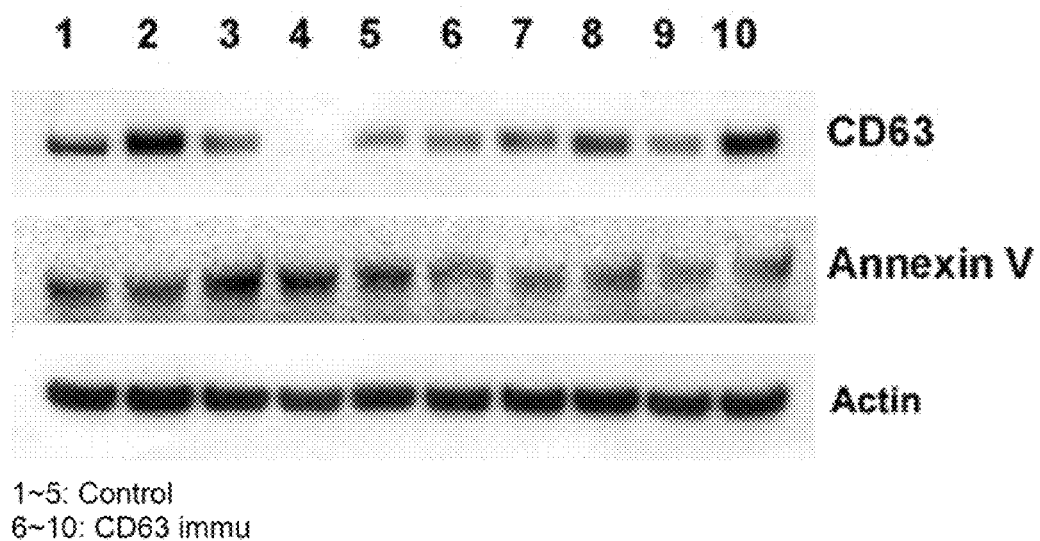

FIG. 8. Western Blot analysis of drusen components in the RPE/choroid from control mice (lanes 1-5) and from mice immunized with CD63 (lanes 6-10).

DETAILED DESCRIPTION

The subject matter disclosed herein is described using several definitions, as set forth below and throughout the application.

Unless otherwise noted, the terms used herein are to be understood according to conventional usage by those of ordinary skill in the relevant art. In addition to the definitions of terms provided below, it is to be understood that as used in the specification, embodiments, and in the claims, "a", "an", and "the" can mean one or more, depending upon the context in which it is used.

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" or "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." For example, a "composition that includes a polypeptide" should be interpreted to mean "a composition that comprises a polypeptide."

As used herein, a "patient" may be interchangeable with a "subject." A patient is an animal that may include a human or non-human animal in need of treatment or vaccination.

A "patient in need thereof" may include a patient having a disease, disorder, or condition that is responsive to vaccination with one or more immunogenic components of drusen (e.g., macular drusen). For example, a "patient in need thereof" may include a patient having macular drusen or diagnosed with macular degeneration. A "patient in need thereof" may include a patient at risk for developing drusen, such as macular drusen, or at risk for developing macular degeneration. The phrase "treating or preventing macular degeneration" includes, but is not limited to, treating or preventing AMD.

As used herein, the phrase "treating or preventing drusen in a patient in need thereof" includes, but is not limited to, preventing or inhibiting the formation of drusen, preventing or inhibiting an increase in the size of existing drusen or the appearance of new drusen, and causing a decrease in the size or amount of drusen in the patient in need thereof. The phrase "treating or preventing drusen in a patient in need thereof" includes but is not limited to, treating or preventing macular drusen in the patient in need thereof.

Drusen

As utilized herein "drusen" (singular, "druse") refers to tiny yellow or white accumulations of acellular material that build up in the eye, particularly in or on Bruch's membrane. The molecular components of drusen include protein markers for autophagy and exosomes. (See Wang et al., (2009) PLoS ONE 4(1): e4160, the content of which is incorporated by reference herein in its entirety). The presence of a relatively few small hard drusen is normal with advancing age, and many middle-aged people (>40 years of age) have some hard drusen. However, the occurrence of larger and more numerous drusen in the macula is a common early sign of AMD. As such, the term "drusen" may include "macular drusen."

Molecular components of drusen may include intracellular proteins, or variants or fragments thereof, selected from a group consisting of nuclear proteins, mitochondrial proteins, cytoplasmic proteins, cytoskeleton proteins, and combinations thereof. Nuclear proteins may include, but are not limited to, histones (e.g., histone H1, histone H2A, histone H2B, histone MAC, histone H2AZ, histone H2A/O, histone 1-12A2, histone H2BF, histone h2bc, histone H3, histone H4, and combinations thereof). Mitochondrial or cytoplasmic proteins may include, but are not limited to aldehyde dehydrogenase 3, aldehyde dehydrogenase 5, ATP synthase α-chain of mitochondria, cell adhesion protein SQM1, creatine kinase b, enolase 2, aldolase (e.g., aldolase A), malate dehydrogenase 1, pyruvate dehydrogenase, pyruvate kinase (e.g., pyruvate kinase of muscle or M1 isozyme), recoverin, lactate dehydrogenase A, protein kinase (cAMP-dependent, catalytic) inhibitor β, glucose phosphate isomerase, cyclophilin A (i.e., peptidylprolyl isomerase A), phosphoglycerate kinase (e.g., GTP or phosphorgylcerate kinase 1), calmodulin 2, G3PDH, dystrobrevin α, phosphoinositide-3-kinase, triosephosphate isomerase (e.g., triosephosphate isomerase 1). 14-3-3 β, apolipoprotein A1, phospholipase A2, myosin, crystallin proteins (e.g., crystallin, $β_s$-crystallin, α-B-crystallin, β-A3-crystallin, β-A4-crystallin, β-B1-crystallin, β-B2-crystallin, and combinations thereof), polyubiquitin, ubiquitin, peroxiredoxin, VEGF, retinoic acid binding protein 3, calreticulin or calreticulin precursor, exosome proteins (e.g., CD63, CD81, LAMP-2), and combinations thereof. Cytoskeleton proteins may include, but are not limited to, actin β, actinin α, vimentin, plectin 1, actin a2, tubulin (e.g., tubulin α1a, tubulin α3, and tubulin β), and combinations thereof.

Molecular components of drusen also may include extracellular proteins such as extracellular matrix proteins, serum proteins, or a protein of unknown origin referred to as "novel leucine-rich protein." Extracellular matrix proteins may include, but are not limited to, clusterin, TIMP3, annexins (e.g., annexin I, annexin II, annexin V, and annexin VI), vitronectin, apolipoprotein E, clathrin, lactalbumin β, collagen type XII α1, annexin 5, HtrA serine peptidase 1, prostasin binding, protease inhibitor 4, integrin β, fibronectin, glycosaminoglycans, and combinations thereof. Serum proteins may include, but are not limited to, complement 3, complement 5, complement 8, complement 9, CFH, Ig α2C, Ig gamma 2C, Ig lambda, albumin, hemoglobin (e.g., hemoglobin β), haptoglobin, haptoglobin-related protein, amyloid P component of serum, transferrin, ceruloplasmin, α-1-microglobulin/bikunin precursor, α-1 antiproteinase, glycoprotein α1β, HLA-DR, MHC II, CD46, CCL2, F4/80, CD11B, ceruloplasmin, plasminogen, and combinations thereof.

In some embodiments, the disclosed pharmaceutical compositions include an effective amount of at least one intracellular polypeptide present in drusen or an immunogenic fragment or variant of the polypeptide that is effective for inducing or eliciting an immune response against the polypeptide. In some embodiments, the polypeptide may be selected from a group consisting of: $β_s$-crystallin; α-B-crystallin; vimentin; calreticulin precursor; cyclophilin A (i.e., peptidylprolyl isomerase A); histone H2A type 1-E; histone cluster 1, H2ai; H2A histone family, member Z; histone cluster 1, H2bb; and combinations thereof, or an immunogenic fragment or variant of the polypeptide that is effective for inducing or eliciting an immune response against the polypeptide.

In some embodiments, the disclosed compositions include human drusen proteins. However, the disclosed compositions may include human or non-human drusen proteins, provided that the drusen proteins in the composition are antigenic in a patient after administration and induce or elicit an immune response against the patient's native drusen protein. For example, the disclosed compositions may include a non-human protein provided that the non-human protein is antigenic in a human patient and induces or elicits an immune response against the human patient's native drusen protein.

As used herein, "$β_s$-crystallin" includes the polypeptide referenced by GenBank Accession No. P22914 (version P22914.4, GI:4033688), alternatively referred to as "beta-crystallin S," "Gamma-crystallin B," and "Gamma-S-crystallin." $β_s$-crystallin may include an amino acid sequence of SEQ ID NO:1.

As used herein, "α-B-crystallin" includes the polypeptide referenced by GenBank Accession No. P02511 (version P02511.2, GI:117385), alternatively referred to as "Alpha-crystallin B chain," "Alpha(B)-crystallin," "Rosenthal fiber component," "Heat shock protein beta-5," and "Renal carcinoma antigen NY-REN-27." α-B-crystallin chain may include an amino acid sequence of SEQ ID NO:2.

As used herein, "vimentin" includes the polypeptide referenced by GenBank Accession No. P08670 (version P08670.4, GI:55977767). Vimentin may include an amino acid sequence of SEQ ID NO:3.

As used herein, calreticulin precursor includes the polypeptide referenced by GenBank Accession No. NP_004343 (version NP_004334.1, GI:4757900). Calreticulin precursor may include an amino acid sequence of SEQ ID NO:4.

As used herein, cyclophilin A alternatively referred to as "peptidylprolyl isomerase A" includes the polypeptide referenced by GenBank Accession No. NP_66953 NP_001008741 (version NP_066953.1, GI:10863927). Cyclophilin A may include an amino acid sequence of SEQ ID NO:5.

As used herein, "Histone H2A type 1-E" includes the polypeptide referenced by GenBank Accession No. P28001 (version P28001.2, GI:121968), alternatively referred to as "H2A.2," and "H2A/a." Histone H2A type 1-E may include an amino acid sequence of SEQ ID NO:6.

As used herein, "histone cluster 1, H2ai" includes the polypeptide referenced by GenBank Accession No. NP_003500 (version NP_003500.1, GI:4504239). Histone cluster 1, H2ai may include an amino acid sequence of SEQ ID NO:7.

As used herein, "H2A histone family, member Z" includes the polypeptide referenced by GenBank Accession No. NP_002097 (version NP_002097.1, GI:4504255). H2A histone family, member Z may include an amino acid sequence of SEQ ID NO:8.

As used herein, "Histone cluster 1, H2bb" includes the polypeptide referenced by GenBank Accession No.

NP_066406 (version NP_066406.1, GI:10800140). Histone cluster 1, H2bb may include an amino acid sequence of SEQ ID NO:9.

As used herein, "CD63" includes the polypeptide referenced by GenBank Accession No. AAP36787 (version AAP36787.1, GI:30585029). CD63 may include an amino acid sequence of SEQ ID NO:10.

Efficacy

As used herein, the phrase "effective amount" shall mean that dosage that provides the specific pharmacological response for which the vaccine or pharmaceutical composition is administered in a significant number of subjects in need of treatment or vaccination. An effective amount of a vaccine or pharmaceutical composition that is administered to a specific subject in a specific instance will not always be effective in treating or preventing the conditions or diseases described herein, even though such dosage is deemed to be a generally effective amount by those of skill in the art. Efficacy of treatment in a subject or patient having AMD may be determined by the guidelines, or a modification of the guidelines, in the Age-Related Eye Disease Study (AREDS) as provided at its website (https://web.emmes.com/study/aredsimop.htm) or by current clinical instruments and methods used by the care giver (e.g., retinal specialist, ophthalmologist or physician) that are being used at the time to assess changes in the retina caused by disease. Tests and methods may include, but are not limited to, vision testing (e.g., via the Snellen chart, where the patient exhibits at least a one, or preferably two, line improvement), the Amsler grid test (e.g., where the patient exhibits improvement in ability to see corners or sides of the grid, where the patient observes fewer wavy lines in the grid, or where the patient observes fewer holes or missing lines in the grid), opthalmoscopy, fundus photography, and fluorescein angiography. Efficacy of treatment in a patient (e.g., a patient having AMD or at risk for developing AMD) may be assessed by observing a decrease in size of drusen (e.g., a decrease in the mass of selected macular drusen of at least about 20%, 30%, 40%, 50%, 60%, 70%, 80%, 90%, or 100%) or a decrease in number of total drusen (e.g., a decrease in number of total macular drusen of at least about 20%, 30%, 40%, 50%, 60%, 70%, 80%, 90%, or 100%). Efficacy of treatment in a patient (e.g., a patient having AMD or at risk for developing AMD) may be assessed by observing the non-occurrence of drusen in the patient (e.g., the non-occurrence of macular drusen in the patient).

An "effective amount" of a polypeptide, a fragment thereof, or a variant thereof, is that amount which when administered to a patient induces or elicits an immune response against a corresponding drusen protein of the patient. Immune responses may include antibody-mediated responses, cell-mediated responses, or both. In order to assess the efficacy of the vaccine or immunogenic composition, the immune response may be assessed by measuring antibody induction to particular epitopes of the drusen protein or by measuring the induction of T-cell responses (e.g., $CD8^+$ responses) against the drusen protein. Antibody responses may be measured by assays known in the art such as Southern Blots and ELISA. T-cell responses may be measured, for example, by using tetramer staining of fresh or cultured PBMC, ELISPOT assays, or by using functional cytotoxic assays, which are well-known to those of skill in the art. In order to assess the efficacy of the vaccine or immunogenic composition, the immune response also may be assessed by observing a decrease in size of drusen (e.g., a decrease in the mass of selected macular drusen of at least about 20%, 30%, 40%, 50%, 60%, 70%, 80%, 90%, or 100%) or a decrease in number of total drusen (e.g., a decrease in number of total macular drusen of at least about 20%, 30%, 40%, 50%, 60%, 70%, 80%, 90%, or 100%). Efficacy of the vaccine or immunogenic composition (e.g., in a patient having AMD or at risk for developing AMD) also may be assessed by observing the non-occurrence of drusen in the patient (e.g., the non-occurrence of macular drusen in the patient).

In some embodiments, the disclosed pharmaceutical compositions may be utilized to illicit an immune response de novo. In further embodiments, the pharmaceutical compositions disclosed herein may be utilized to "potentiate" or "enhance" an immune response. As used herein, "potentiating" or "enhancing" an immune response means increasing the magnitude or the breadth of the immune response. For example, the number of cells that recognize a particular epitope may be increased ("magnitude") or the numbers of epitopes that are recognized may be increased ("breadth") (e.g., 5-fold, or 10-fold relative to a reference composition).

Formulation and Delivery of the Compositions

The pharmaceutical compositions disclosed herein include at least one immunogenic component for inducing or eliciting an immune response against a component of drusen. The disclosed compositions may be utilized as vaccines or immunogenic compositions for treating or preventing drusen formation or macular degeneration. The terms "vaccine" and "immunogenic composition" are defined herein in a broad sense to refer to any type of biological agent in an administratable form capable of stimulating an immune response in an animal inoculated with the vaccine or immunogenic composition. An immune response may include induction of antibodies or induction of a T-cell response. Herein, the term "protection" when used in reference to an immunogenic composition or vaccine refers to the amelioration (either partial or complete) of any of the signs or symptoms associated with the disease or condition in question.

The pharmaceutical compositions disclosed herein include at least one immunogenic component for inducing or eliciting an immune response against a component of drusen (e.g., a component of macular drusen). Immunogenic components may include polypeptides, carbohydrates, or lipid components. In some embodiments, immunogenic components include polypeptides, or variants or fragments thereof, which normally are found intracellularly (e.g., intracellular nuclear, mitochondrial, structural, or cytoplasmic proteins) or which are not normally found extracellularly (e.g., proteins which are not found on the cell surface membrane, the extracellular matrix, or are not observed to circulate in blood).

As used herein, a "polypeptide," "peptide," or "protein" means a linear series of amino acid residues, which may be naturally-occurring or modified amino acid residues, connected one to the other by peptide bonds between the alpha-amino and carboxy groups of adjacent residues. "Polypeptides," "peptides," or "proteins" may be modified (e.g., via processes including glycosylation, myristoylation, conjugation, and the like). A "peptide" has a relatively short amino acid sequence compared to a "polypeptide" or a "protein." The terms "polypeptide" and "protein" may be utilized interchangeably herein.

The disclosed pharmaceutical compositions may include a polypeptide present in drusen or an immunogenic fragment or variant of the polypeptide that is glycosylated or non-glycosylated and that induces or elicits an immune response against the polypeptide present in drusen. The polypeptide of the composition may be recombinant.

The disclosed pharmaceutical compositions may include the full-length polypeptide or an immunogenic fragment or variant thereof that induces or elicits an immune response against the full-length polypeptide. An immunogenic fragment may include a polypeptide having at least 10 contiguous amino acids of the full-length polypeptide (or at least 15, 20, 25, 50, 100, 200, or 400 contiguous amino acids of the full-length polypeptide). For example, a contiguous ten amino acid fragment may include an amino acid sequence 1-10 of any of SEQ ID NOS:1-10 (or an amino acid sequence 2-11 of any of SEQ ID NOS:1-10, or an amino acid sequence 3-12 of any of SEQ ID NOS:1-10, etc.). Optionally, a fragment may retain one or more biological activities of a reference polypeptide. Preferably, the fragment is immunogenic and induces or elicits an immune response against at least one epitope of the full-length polypeptide.

The disclosed pharmaceutical compositions may include an effective amount of at least one variant of a polypeptide present in drusen or an immunogenic fragment of the variant, where the variant or fragment thereof induces or elicits an immune response against the polypeptide present in drusen. A variant may include a polypeptide having significant sequence identity to a reference polypeptide. For example, a variant may include a polypeptide having at least about 95% amino acid sequence identity to a reference polypeptide (e.g., a polypeptide having at least about 95% amino acid sequence identity to a polypeptide of any of SEQ ID NOS:1-10), which sequence identity may be determined by methods known in the art (e.g., using the BLAST algorithm software provided at the website for the National Center for Biotechnology Information). A variant may have deletions, insertions, or amino acid substitutions relative to a reference polypeptide. Amino acid substitutions may include conservative amino acid substitutions (e.g., D<->E, K<->R, S<->T, and the like) or non-conservative amino acid substitutions. A variant may include a fusion polypeptide, where the fusion polypeptide includes: (a) a portion derived from a polypeptide present in drusen or a fragment thereof (e.g., at least a ten (10) contiguous amino acid sequence of a polypeptide present in drusen), fused at the N-terminus, C-terminus, or both, to; (b) a heterologous portion (i.e., a portion not derived from a polypeptide present in drusen). A fusion polypeptide may include a polypeptide that is biotinylated or fused to a hapten. Optionally, a variant may retain one or more biological activities of a reference polypeptide or the variant induces or elicits an immune response against at least one epitope of the reference polypeptide after the variant is administered to a patient.

The pharmaceutical compositions may include a polypeptide, or a variant or fragment thereof, that has been modified to enhance immunogenicity. For example, the polypeptide may be conjugated or fused to one or more haptens.

The disclosed pharmaceutical compositions typically include a polypeptide, or a variant or fragment thereof, at a concentration sufficient to induce or elicit an immune response (e.g., antibody induction, a T-cell response, or both) against the polypeptide. In some embodiments, the disclosed pharmaceutical compositions may include at least about 10 μg of the polypeptide, or a variant or fragment thereof (or at least about 20, 40, 60, 80, or 100 μg of the polypeptide, or a variant or fragment thereof). In other embodiments, the immunogenic composition or vaccine includes about 1-1000 μg (preferably about 10-100 μg) of a polypeptide present in drusen or an immunogenic fragment or variant thereof.

The pharmaceutical compositions may be monovalent or polyvalent. The pharmaceutical compositions may include an effective amount of at least one polypeptide present in drusen, or an immunogenic fragment or variant of the polypeptide for inducing or eliciting an immune response against the polypeptide. Suitable polypeptides may include, but are not limited to: $\beta_s$-crystallin; $\alpha$-B-crystallin; vimentin; calreticulin precursor; cyclophilin A (i.e., peptidylprolyl isomerase A), or an immunogenic fragment or variant of the polypeptide. The pharmaceutical composition further may include an additional polypeptide present in drusen other than $\beta_s$-crystallin; $\alpha$-B-crystallin; vimentin; calreticulin precursor; and cyclophilin A (i.e., peptidylprolyl isomerase A); or an immunogenic fragment or variant of the additional polypeptide. For example, the compositions may include another drusen protein on non-drusen protein as disclosed herein or as known in the art.

The disclosed pharmaceutical compositions may include a panel or plurality of immunogenic components for inducing or eliciting immune responses against drusen components. For example, the compositions may include a panel or plurality of macular drusen polypeptides or immunogenic fragments or variants thereof that induce or elicit an immune responses against the drusen polypeptides. As used herein, a "panel" or "plurality" of components means two or more separate and different components (e.g., two or more separate and different polypeptides).

The pharmaceutical compositions disclosed herein may be formulated as vaccines for administration to a subject in need thereof. Such compositions can be formulated or administered in dosages and by techniques well known to those skilled in the medical arts taking into consideration such factors as the age, sex, weight, and condition of the particular patient, and the route of administration.

The disclosed pharmaceutical compositions may be formulated for delivery in any suitable manner. For example, the compositions may be formulated for at least one of intramuscular delivery, subdermal delivery, subcutaneous delivery, ocular delivery, oral delivery, intravenous delivery, intraperitoneal delivery, intranasal delivery, or pulmonary delivery.

The pharmaceutical compositions disclosed herein may be delivered via a variety of routes. Typical delivery routes include parenteral administration (e.g., intradermal, intramuscular or subcutaneous delivery). Other potential routes of delivery include ocular administration, oral administration, intranasal administration, pulmonary administration, intravaginal administration, and intrarectal administration. Formulations of the pharmaceutical compositions may include liquid formulations for parenteral, subcutaneous, intradermal, intramuscular, intravenous, or ocular administration (e.g., injectable administration) such as sterile solutions, suspensions, or emulsions. Formulations of the pharmaceutical compositions also may include liquid formulations (e.g., topical formulations or ingestible formulations) for ocular, oral, nasal, anal, and vaginal administration, including solutions, suspensions, syrups or elixirs. The vaccines may be lyophilized prior to delivery and reconstituted prior to administration.

It is generally advantageous to formulate the present compositions in dosage unit form for ease of administration and uniformity of dosage. "Dosage unit form" as used herein refers to physically discrete units suitable as unitary dosages for a patient; each unit containing a predetermined quantity of the active material calculated to produce the desired therapeutic effect in association with the required pharmaceutical carrier, excipient, or diluent. The specification for the dosage unit forms are dictated by and depend on among other factors (a) the unique characteristics of the active material and the particular therapeutic effect to be achieved; (b) the limitations inherent in the art of compounding such active material for the treatment of disease; and (c) the manner of intended administration of the dosage unit form. In some embodiments, a dose of the immunogenic composition or vaccine includes at least about 10 μg (or at least about 20, 40, 60, 80, or 100 μg) of a polypeptide present in drusen or an immunogenic fragment or variant thereof. In other embodiments, a dose of the immunogenic composition or vaccine includes about 1-1000 µg (preferably about 10-100 µg) of a polypeptide present in drusen or an immunogenic fragment or variant thereof.

The present immunogenic composition and vaccines may be formulated with a pharmaceutically acceptable carrier, excipient, or diluent. The forms suitable for injectable commonly include sterile aqueous solutions (where water soluble) or dispersions and sterile powders for the extemporaneous preparation of sterile injectable solutions or dispersion. The formulation should desirably be sterile and fluid to the extent that it can be delivered easily with a syringe. The dosage form should be stable under the conditions of manufacture and storage and typically is preserved against the contaminating action of microorganisms such as bacteria and fungi. The carrier, excipient, or diluent can be a solvent or dispersion medium containing, for example, water, ethanol, polyol (for example, glycerol, propylene glycol, liquid polyethylene glycol, and the like), suitable mixtures thereof and vegetable oils. One possible carrier, excipient, or diluent is a physiological salt solution. The proper fluidity of the solution can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal (sodium ethylmercuri-thiosalicylate), deomycin, gentamicin and the like. In many cases it may be preferable to include isotonic agents, for example, sugars or sodium chloride. Prolonged absorption of the injectable compositions, if desired, can be brought about by the use in the compositions of agents delaying absorption, for example, aluminum monostearate and gelatin.

Sterile solutions may be prepared by incorporating a desired amount of the polypeptide in an appropriate solvent, optionally with various amounts of the other ingredients enumerated above, as required, followed by filtered sterilization. Generally, dispersions can be prepared by incorporating the various active ingredients into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient (i.e., lyophilized form of the active ingredient) plus any additional desired ingredient from a previously sterile-filtered solution thereof.

It may also be advantageous to add a stabilizer to the present compositions. Suitable stabilizers include, for example, glycerol/EDTA, carbohydrates (such as sorbitol, mannitol, trehalose, starch, sucrose, dextran or glucose), proteins (such as albumin or casein) and protein degradation products (e.g., partially hydrolyzed gelatin). If desired, the formulation may be buffered by methods known in the art, using reagents such as alkali metal phosphates, e.g., sodium hydrogen phosphate, sodium dihydrogen phosphate, potassium hydrogen phosphate or potassium dihydrogen phosphate. Other solvents, such as ethanol or propylene glycol, can be used to increase solubility of ingredients in the vaccine formulation or the stability of the solution. Further additives which can be used in the present formulation include conventional antioxidants and conventional chelating agents, such as ethylenediamine tetraacetic acid (EDTA).

The pharmaceutical compositions may be administered prophylactically or therapeutically. For example, in prophylactic administration the vaccines may be administered in an amount sufficient to induce $CD8^+$, $CD4^+$, or antibody responses for preventing drusen formation or macular degeneration. In another example, in therapeutic applications the vaccines may be administered to a patient in an amount sufficient to induce or elicit a therapeutic effect (e.g., $CD8^+$, $CD4^+$, or antibody responses to the drusen immunogenic components, which reduces drusen formation or macular degeneration or at least partially arrests or slows drusen formation or macular degeneration (i.e., as a "therapeutically effective dose")).

The compositions included in the vaccine regimen of the invention can be co-administered or sequentially administered with other immunological, immunogenic or vaccine or therapeutic compositions. The compositions may be co-administered or sequentially administered with an adjuvant or other therapeutic or prophylactic agent. For example, the disclosed compositions may be administered together with additional agents for treating or preventing drusen in a patient in need thereof. Furthermore, the disclosed compositions may be administered together with additional agents for treating or preventing AMD in a patient in need thereof. Additional agents for treating or preventing AMD may include, but are not limited to, anti-angiogenic agents such as pegaptanib (e.g., pegaptanib sodium injection sold under the tradename Macugen®), bevacizumab sold under the tradename Avastin®), and ranibizumab (e.g., sold under the tradename Lucentis®).

Adjuvants

The term "adjuvant" refers to a compound or mixture that is present in a vaccine and enhances the immune response to an antigen present in the vaccine. For example, an adjuvant may enhance the immune response to a polypeptide present in a vaccine as contemplated herein, or to an immunogenic fragment or variant thereof as contemplated herein. An adjuvant can serve as a tissue depot that slowly releases the antigen and also as a lymphoid system activator that non-specifically enhances the immune response. Examples of adjuvants which may be employed include MPL-TDM adjuvant (monophosphoryl Lipid A/synthetic trehalose dicorynomycolate, e.g., available from GSK Biologics). Another suitable adjuvant is the immunostimulatory adjuvant AS021/AS02 (GSK). These immunostimulatory adjuvants are formulated to give a strong T cell response and include QS-21, a saponin from *Quillay saponaria*, the TL4 ligand, a monophosphoryl lipid A, together in a lipid or liposomal carrier. Other adjuvants include, but are not limited to, nonionic block co-polymer adjuvants (e.g., CRL 1005), aluminum phosphates (e.g., $AlPO_4$), R-848 (a Th1-like adjuvant), imiquimod, PAM3CYS, poly (I:C), loxoribine, potentially useful human adjuvants such as BCG (bacille Calmette-Guerin) and *Corynebacterium parvum*, CpG oligodeoxynucleotides (ODN), cholera toxin derived antigens (e.g., CTA 1-DD), lipopolysaccharide adjuvants, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

Prime-Boost Vaccination Regimen

The disclosed composition may be administered as vaccines utilizing a selected "prime-boost vaccination regimen." As used herein, a "prime-boost vaccination regimen" refers to a regimen in which a subject is administered a first composition one or more times (e.g., one time or two or three times with about 2, 3, or 4 weeks between administrations) and then after a determined period of time after having administered the first composition (e.g., about 2 weeks, about 4 weeks, about 2 months, about 3 months, about 4 months, about 5 months, about 6 months, or longer), the subject is administered a second composition. The second composition may also be administered more than once, with at least 2, 3, or 4 weeks between administrations. The first and second compositions may be the same or different.

Methods and Kits

The disclosed compositions may be utilized in methods for immunizing a patient against one or more components of drusen. The methods disclosed herein may include administering the disclosed compositions to an animal (e.g., a human). The methods may be effective for treating or preventing drusen (e.g., macular drusen) in a patient in need thereof. The disclosed compositions may also be utilized in methods for inhibiting accumulation of drusen proteins extracellularly in the region of the retinal pigment epithelium and choroid of a patient in need thereof. The methods disclosed herein may be effective for treating or preventing macular degeneration (e.g., AMD) in a patient in need thereof.

Kits are also contemplated herein including kits for administering the disclosed compositions and kits for making the disclosed compositions. The kits may include one or more components for performing the administration methods disclosed herein. For example, the kits may include one or more of the vaccine or pharmaceutical compositions disclosed herein or components for making or administering the vaccine or pharmaceutical compositions disclosed herein. The vaccine or pharmaceutical compositions or components may be provided in any suitable form (e.g., liquid form or lyophilized form). Kits further may include solvents for resuspending or dissolving a lyophilized protein.

EXAMPLES

The following examples are illustrative and are not intended to limit the scope of the claimed subject matter.

Introduction and Strategy

Age-related Macular Degeneration (AMD) is a progressive degeneration of the macula of the retina, usually bilateral, leading to a severe decrease in fine vision and a central scotoma in the elderly. AMD is broadly classified as either dry (non-neovascular) or wet (neovascular). The dry form of AMD, which is characterized by drusen in the macula, is more common and accounts for about 85 to 90% of patients with AMD. Patients with dry AMD have a substantial risk of developing wet AMD.

The formation of drusen, an extracellular, amorphous deposit of material on Bruch's membrane in the macula of the retina, occurs early in the course of the pathogenesis of AMD. Drusen is an extracellular deposit associated with Bruch's membrane and the deposition of drusen in the macula is a key factor in the etiology of AMD. The composition of drusen has been studied by proteomics, histology and immunohistochemistry. Apparently, drusen contains a wide variety of molecules, including proteins that have been contributed from the retinal pigment epithelium (RPE), choroidal vasculature endothelia and the blood. Proteins that are present in drusen normally are present in the nucleus, mitochondria, cytoplasm, cytoskeleton, extracellular matrix and serum.

Mouse models were used to test whether immunization against specific components of drusen can stimulate an immune response that prevents the accumulation of or reduces the amount of proteins, and perhaps other molecules, that are found in drusen-like material around Bruch's membrane. Intracellular nuclear, mitochondrial or cytoplasmic proteins were selected as candidates for inducing drusen-specific immune responses in the mouse models based on the hypothesis that immunization with these proteins may be less likely to cause damage to other tissues because the intracellular proteins are accessible to immune cell activity only when exposed in a pathological, extracellular states, such as in drusen. Furthermore, when the intracellular proteins found in drusen are excreted from the cell, these proteins may be the "nucleating factors" which cause the formation of drusen that then "attracts" otherwise commonly present extracellular proteins and blood proteins. Extracellular proteins and blood proteins may not form drusen unless intracellular proteins are present extracellularly.

Thus, by removing these proteins via an immune response, these proteins and other proteins associated with these removed proteins may be decreased in the environment around Bruch's membrane. The formation of drusen therefore may be inhibited or prevented. This immunotherapy approach may lead to a novel therapeutic treatment for AMD by modulating the formation of drusen.

Methods

Group 1: Immunization of AMD Model Mice-APOE (Males)

Transgenic APOE4 male mice (001549-M-M, homozygous, B6.129P2-Apoe$^{tm3\ (APOE4)\ Mae}$ N8, purchased from Taconic Farms, Inc.) were put on a high fat cholesterol-rich diet (HFD) starting at 18 mos of age. These animals are considered a model for the changes that can occur in human AMD (Malek G. et al., "Apolipoprotein E allele-dependent pathogenesis: a model for age-related macular degeneration." Proc Natl Acad Sci USA. 2005; 102:11900-11905, which is incorporated by reference herein in its entirety). The animals were kept on the HFD diet for 3 mos. 10 mice were randomized to two arms: Arm #1 (4 mice). 50 µg Complete Freund's Adjuvant (CFA) (Sigma-Aldrich, Inc.) was used for initial injections and 50 µg Incomplete Freund's Adjuvant (IFA) (Sigma-Aldrich, Inc.) for subsequent boosters. Arm #2 (6 mice). 10 µg bovine $\beta_s$-crystallin (Sigma-Aldrich, Inc.) containing 50 µg CFA was used for initial injections and 10 µg bovine $\beta_s$-crystallin containing 50 µg WA for subsequent boosters. Bovine $\beta_s$-crystallin and murine βs-crystallin exhibit 96% sequence identity (comparing GenBank Accession No. AAA30401.1 to NCBI Reference Sequence No. NP_034095.1 via the blastp algorithm available from the National Center for Biotechnology Information at its website).

The time table for Arms #1 and 2 was as follows:

Day 1: Initial immunization
Day 22: Booster 1
Day 33: Start HFD and continue to the day of sacrifice
Day 43: Booster 2
Day 50: Bleed 1 to check antibody titer
Day 64: Booster 3
Day 85: Booster 4
Day 92: Bleed 2 to check antibody titer
Day 106: Booster 5
Day 125: Bleed 3 to check antibody titer
Day 127: Sacrificed animals for Western blots (WB) and Immunohistochemistry (IHC).

Group 2: Immunization of AMD Model Mice-APOE (Females)

Transgenic APOE4 female mice (001549-M-F, homozygous, B6.129P2-Apoe$^{tm3\ (APOE4)\ Mae}$ N8, purchased from Taconic Farms, Inc.) were put on a high fat cholesterol-rich diet starting at 18 mos of age. The animals were kept on the HFD diet for 3 mos. 11 mice were randomized to two arms:

Arm #1 (3 mice): 50 μg CFA was used for initial injections and 50 μg IFA for subsequent boosters; Arm #2 (8 mice): 50 μg CFA and a mixture of antigens were used for initial injections and 50 μg IFA and a mixture of antigens for subsequent boosters. The mixture of antigens contained 10 μg bovine crystallin (Sigma-Aldrich, Inc.), 50 μg murine αB crystallin (Bio-Synthesis, Inc.), 50 μg murine calreticulin (Bio-Synthesis, Inc.), 50 μg murine vimentin (Bio-Synthesis, Inc.) and 50 μg murine cyclophilin A (Bio-Synthesis, Inc.).

The time table for Arms #1 and 2 was as follows:

Day 1: Initial immunization
Day 22: Booster 1
Day 29: Start HFD and continue to the day of sacrifice
Day 43: Booster 2
Day 50: Bleed 1 to check antibody titer
Day 64: Booster 3
Day 85: Booster 4
Day 92: Bleed 2 to check antibody titer
Day 106: Booster 5
Day 109: Bleed 3 to check antibody titer
Day 110: Sacrificed animals for WB and IHC.

Group 3: Immunization of Old Mice with CD63

Animal models for AMD utilizing old mice have been described. (See Wang et al., (2009) PLoS ONE 4(1): e4160, the content of which is incorporated by reference herein in its entirety). C57BL/6 male mice (Harlan Laboratories, Inc.) were used for immunization procedures starting at 18 mos of age. Twenty mice were randomized equally to two arms: Arm #1 (10 mice). Fifty μg CFA was used for initial injections and 50 μg IFA for subsequent boosters; Arm #2 (10 mice). Fifty μg CFA and murine CD63 (Bio-Synthesis, Inc.) were used for initial injections and 50 μg IFA and CD63 for subsequent boosts.

The time table for Arms #1 and 2 was as follows:

Day 1: Initial immunization
Day 22: Booster 1
Day 43: Booster 2
Day 50: Bleed 1 to check antibody titer
Day 64: Booster 3
Day 85: Booster 4
Day 92: Bleed 2 to check antibody titer
Day 106: Booster 5
Day 127: Booster 6
Day 134: Bleed 3 to check antibody titer
Day 147: Sacrificed animals for WB.

Serum Antibody Levels

The collected sera from the tail vein of each mouse was immediately frozen and stored at −80° C. until assayed by direct ELISA for antibody titer. Ninety-six well plates (Costar® EIA/RIA, VWR International, LLC) were coated with 50 μl of target protein (4 mg/ml in 50 mM carbonate buffer, pH 10.4) and incubated overnight at 4° C. Blocking was done with 100 μl of 1% normal rabbit serum in carbonate buffer overnight at 4° C. followed by three washings with PBS/ 0.01% Tween-20. The serum test samples were serially diluted and 100 μL added to each well. The plates were sealed and incubated at room temperature for 1 hr. After three washes with PBS/Tween (100 μl/well), the detection antibody (Goat anti-mouse, all IgG, IgM) HRP conjugate at 1:5000, 50 μl/well) was added, and the plates were incubated 1 hr at room temperature in a humidified box. After three washes with PBS/Tween, followed by addition of 50 μl of developing reagent to each well, plates were incubated in the dark for 30 min. The reaction was stopped with 1 N $H_2SO_4$. Plates were read at OD 450 nm in a plate reader. Data was imported into Excel for analyses of the antigens with an appropriate immunological response Western Blot (WB)

RPE/Choroid was dissected, lysed in buffer (20 mM HEPES, pH 7.0, mM KCl, 2 mM $MgCl_2$, 0.5% Nonidet P-40, 1 mM $Na_3VO_4$, 1 mM PMSF, and 0.15 U/ml aprotinin) and homogenized. Protein concentrations were determined using the Bradford colorimetric assay. Thirty micrograms of each protein lysate were loaded in each lane in sample buffer (2% SDS, 10% glycerol, 0.001% bromophenol blue, 1% DTT, and 0.05 M Tris-HCl, pH 6.8), separated on 10% SDS-PAGE (Invitrogen Corporation), and transferred to a PVDF membrane (Millipore Corporation). The blots were blocked with 5% nonfat milk in PBS for 1 hr and incubated with mouse anti-$\beta_s$-crystallin (1:1000), mouse anti-αB crystallin (1:200, Stressgen Bioreagents Corporation), rabbit anti-fibronectin (1:200, Santa Cruz Biotechnology, Inc.), rabbit anti-moesin (1:1000, Cell Signaling Technology, Inc.), rabbit anti-polyubiquitin (1:1000, Abcam Plc.), mouse anti-CD63, rabbit anti-annexin V, followed by peroxidase-conjugated donkey anti-mouse or rabbit IgG (1:15,000) for 1 hr at room temperature. Finally, the blots were developed by enhanced chemiluminescence (ECL) (Pierce Chem. Co.) on Hyperfilm® brand film (Amersham Corporation).

Immunohistochemistry (IHC)

Enucleated eyes from mice were fixed in 2% wt/vol paraformaldehyde in 0.01 M phosphate buffered saline (PBS; pH 7.4) at 4° C. overnight. Immunohistochemistry was performed on paraffin sagittal sections of the retinas for the primary antibodies overnight at 4° C. Primary antibodies included anti-$\beta_s$-crystallin (1:50), anti-αB crystallin (1:50, Stressgen Bioreagents Corporation), anti-fibronectin (1:50, Santa Cruz Biotechnology, Inc.), anti-moesin (1:50, Cell Signaling Technology, Inc.), anti-polyubiquitin (1:500, Abcam Plc.). Primary antibody was omitted in the negative control. After several washes, tissue sections were incubated with the secondary antibody, anti-mouse rhodamine red (1:1000, Molecular Probe® Dyes, Invitrogen Corporation) for 1 hr at room temperature. After washing with PBS, the slides were mounted with Vectorshield containing 4',6-diamidino-2-phenylindole (DAPI) (Vector Laboratories Co.) and observed using confocal microscopy.

Results

Group 1: Anti-$\beta_s$-Crystallin Antibody Titers, ELISA:

Mice were immunized with CFA alone (controls, Arm #1) or $\beta_s$-crystallin in CFA (Arm #2) day 0. Booster compositions included $\beta_s$-crystallin in IFA (Arm #2) or IFA alone (Arm #1) and were administered approximately every three weeks for a total of 6 injections/mouse. The final immunizations were given 21 d before the mice were sacrificed. $\beta_s$-crystallin-specific antibody titer was determined on the collected sera for mice in Arms #1 and #2. (See FIG. 1.)

Titers of antibody to $\beta_s$-crystallin in Arm #2 (i.e., in mice immunized with $\beta_s$-crystallin) were more than ten times higher than titers in naive mice or control mice immunized with CFA/IFA. FIG. 1 shows that administering $\beta_s$-crystallin induces an antibody-mediated immune response. There were no immune responses to $\beta_s$-crystallin observed in mice #793, #794, #795, and #797. In contrast, there were strong immune responses to $\beta_s$-crystallin observed in mice #798, #799, #800, #801, #802, and #803.

Group 1: Western Blot

Protein levels of drusen components in the RPE/choroid from mice from Arms #1 and 112 were determined using specific antibodies against $\beta_s$-crystallin, αB crystallin, fibronectin, ubiquitin and moesion. As shown in FIG. 2, the western blots for two control animals from Arm #1 (lanes 1 and 2) were positive for $\beta_s$-crystallin, $\alpha$B crystallin, fibronectin, ubiquitin and moesin. However, most mice immunized against $\beta_s$-crystallin (lanes 3, 4, 5 and 6) had significantly less $\beta_s$-crystallin, $\alpha$B crystallin, fibronectin, ubiquitin and moesion. The western blots show that for mice in Arm #2, 4/4 mice had decreased $\beta_s$-crystallin, $\alpha$B crystallin and fibronectin, and 3/4 mice had decreased ubiquitin and moesion. Actin is an intracellular protein used as an internal standard to show that the loading of the gels for WB was uniform.

Group 1: Immunohistochemistry

To observe the immunization effects, the tissue locations of certain proteins were visualized by immunohistochemistry with specific antibodies to $\beta_s$-crystallin, $\alpha$B crystallin, fibronectin, ubiquitin and moesion. As shown in FIG. 3, there were markedly less depositions of drusen components in the region of Bruch's membrane in the group with high antibody titers to $\beta_s$-crystallin (HFD+Immun), Arm #2) compared with the control group (HFD, Arm #1). Overall, 2/2 mice (4 eyes) had decreased $\beta_s$-crystallin, $\alpha$B crystallin and fibronectin, and 1/2 mice (2 eyes) had decreased ubiquitin and moesin in the region of Bruch's membrane.

Group 1: Conclusions

Transgenic APOE4 mice on HFD accumulate $\beta_s$-crystallin, $\alpha$B crystallin, fibronectin, ubiquitin and moesion in the region of Bruch's membrane as they age, as seen in the immunization control animals. The accumulation of these proteins in mice can be considered similar to the formation of drusen in the human eye. Immunization against $\beta_s$-crystallin led to high circulating antibodies to $\beta_s$-crystallin in transgenic APOE4 mice on FWD. Transgenic APOE4 mice with high circulating antibodies to $\beta_s$-crystallin had less accumulation of $\beta_s$-crystallin, $\alpha$B crystallin, fibronectin, ubiquitin and moesion in the region of Bruch's membrane as they aged. Decreased accumulation of these proteins was demonstrated by both Western blot and immunohistochemistry. These findings suggest that the $\beta_s$-crystallin-antibody reaction led to less deposition of $\beta_s$-crystallin in the region of Bruch's membrane as well as less deposition of other intracellular proteins, $\alpha$B crystallin, fibronectin, ubiquitin and moesion, in the region of Bruch's membrane. In addition, there were likely other untested proteins that also exhibit decreased deposition in the region of Bruch's membrane.

$\beta_s$-crystallin, $\alpha$B crystallin, fibronectin, ubiquitin and moesion are all components of human drusen. Therefore, these results suggest that immunization against certain intracellular proteins of drusen, for example $\beta_s$-crystallin, reduces the deposition of other drusen proteins on Bruch's membrane. Furthermore, these results suggest that immunization against certain intracellular proteins, for example $\beta_s$-crystallin, may prevent or decrease the accumulation of drusen in human subjects.

Group 2: Antibody Titers, ELISA:

Mice were immunized with CFA alone (controls, Arm #1) or $\beta_S$-crystallin, $\alpha$B crystallin, calreticulin, vimentin and cyclophilin A in CFA (Arm #2) day 0. Booster compositions included $\beta_s$-crystallin, $\alpha$B crystallin, calreticulin, vimentin and cyclophilin A in IFA (Arm #2) or IFA alone (Arm #1) and were administered approximately every three weeks for a total of 6 injections/mouse. The final immunizations were given 4 d before the mice were sacrificed. $\beta_s$-crystallin, $\alpha$B crystallin, calreticulin, vimentin and cyclophilin A-specific antibody titers were determined on the collected sera for mice in Arms #1 and #2. (See FIG. 4.)

Titers of antibody to $\beta_s$-crystallin, $\alpha$B crystallin, calreticulin, vimentin and cyclophilin A in Arm #2 were more than five times higher than titers in naïve mice or control mice immunized with CFA/IFA. FIG. 4 shows that administering $\beta_s$-crystallin induces a relatively strong antibody-mediated immune response; whereas, administering $\alpha$B crystallin, calreticulin and vimentin induces a lesser antibody-mediated immune response. There were no immune responses to $\beta_s$-crystallin, $\alpha$B crystallin, calreticulin, vimentin and cyclophilin A observed in mice #807, #811, and #817. In contrast, strong immune responses to $\beta_s$-crystallin were observed for mice #805, #806, #808, #809, #812, #815, #816, and #818. (See FIG. 4A.) Lesser immune responses to $\alpha$B crystalline were observed for mice #809, #812, and #815. (See FIG. 4B.) Lesser immune responses to vimentin also were observed for mice #816 and #818. (See FIG. 4D.) Moderate immune responses to calreticulin were observed for mice #805, #806, #815 and #818. (See FIG. 4E.) No immune response to cyclophyllin A was observed. (See FIG. 4C.)

Group 2: Western Blot

Protein levels of drusen components in the RPE/choroid from mice from Arms #1 and #2 were determined using specific antibodies against $\beta_s$-crystallin, $\alpha$B crystallin, fibronectin, ubiquitin and moesion. As shown in FIG. 5, the western blots for two control animals from Arm 41 (lanes 1 and 2) were positive for $\beta_s$-crystallin, $\alpha$B crystallin, fibronectin, polyubiquitin and moesin. However, most mice immunized against $\beta_s$-crystallin (lanes 3, 4, 5, 6 and 7) had significantly less $\beta_s$-crystallin, $\alpha$B crystallin, fibronectin, polyubiquitin and moesin. The western blots show that for mice in Arm #2, 5/5 mice had decreased $\beta_s$-crystallin and $\alpha$B crystallin, 4/5 mice had decreased fibronectin, and 3/5 mice had decreased moesion and polyubiquitin. Actin is an intracellular protein that was used as an internal standard to show that the loading of the gels for WB was uniform.

Group 2: Immunohistochemistry

To observe the immunization effects, the tissue locations of certain proteins were visualized by immunohistochemistry with specific antibodies to $\beta_s$-crystallin, $\alpha$B crystallin, fibronectin, ubiquitin and moesion. As shown in FIG. 6, there were markedly less depositions of drusen components in the region of Bruch's membrane in the group with high antibody titers to $\beta_s$-crystallin (HFD+Immun), Arm #2) compared with the control group (HFD, Arm #1). Overall, 3/3 mice (6 eyes) had decreased $\beta_s$-crystallin, $\alpha$B crystallin and fibronectin, and 2/3 mice (4 eyes) had decreased moesion and polyubiquitin in the region of Bruch's membrane.

Group 2: Conclusions

The results from Group 2, using slightly different methods from Group 1, reproduce the results from Group 1. The immunized mice in Group 2 were immunized with a mixture of antigens, including $\beta_s$-crystallin, $\alpha$B crystallin, calreticulin, vimentin and cyclophilin A. Immunization against this mixture led to high circulating antibodies against $\beta_s$-crystallin in transgenic APOE4 mice. The other antigens were not as effective at inducing antibodies. However, it is possible that these antigens alone or in some combination with other antigens could produce high circulating antibodies and have effects similar to immunization with $\beta_s$-crystallin. It is also possible that even lesser levels of circulating antibodies against $\alpha$B crystallin, calreticulin and vimentin aided in the reduction of deposition of $\beta_s$-crystallin, $\alpha$B crystallin, fibronectin, ubiquitin and moesion in the region of Bruch's membrane in our experiments.

Transgenic APOE4 mice with high circulating antibodies to $\beta_s$-crystallin had less accumulation of $\beta_s$-crystallin, $\alpha$B crystallin, fibronectin, ubiquitin and moesion in the region of Bruch's membrane as they aged. Decreased accumulation of these proteins was demonstrated by both Western blot and immunohistochemistry. These findings may indicate that the $\beta_s$-crystallin-antibody reaction led to less deposition of $\beta_s$-crystallin in the region of Bruch's membrane as well as less deposition of other intracellular proteins, including αB crystallin, fibronectin, ubiquitin and moesion, in the region of Bruch's membrane. In addition, there were likely other untested proteins that also exhibit decreased deposition.

$\beta_s$-crystallin, αB crystallin, fibronectin, ubiquitin and moesion are all components of human drusen. Therefore, these results suggest that immunization against certain intracellular proteins of drusen, for example $\beta_s$-crystallin, reduces the deposition of other drusen proteins on Bruch's membrane. Furthermore, these results suggest that immunization against certain intracellular proteins, for example $\beta_s$-crystallin, will prevent or decrease the accumulation of drusen in human subjects.

Group 3: CD63 Titers, ELISA:

Mice were immunized with CFA alone (controls, Arm #1) or CD63 in CFA (Arm #2) day 0. Booster compositions included CD63 in IFA (Arm #2) or IFA alone (Arm #1) and were administered approximately every three weeks for a total of 6 injections/mouse. The final immunizations were given 20 d before the mice were sacrificed. CD63-specific antibody titers were determined on the collected sera for mice in Arms #1 and #2. (See FIG. 7.)

Titers of antibody to CD63 in Arm #2 were more than ten times higher than titers in naive mice or control mice immunized with CFA/IFA. FIG. 7 shows that CD63 induces an antibody-mediated immune response. There were no immune responses to CD63 observed in mice #1, #2, #3, #4, #5, #6, #7, #8, #9, and #10. In contrast, strong immune responses to CD63 were observed in mice #30, #31, #32, #33, #36, #38, #41, #42, #43, and #44.

Group 3: Western Blot

Protein levels of drusen components in the RPE/choroid from mice from Arms #1 and #2 were determined using specific antibodies against CD63, $\beta_s$-crystallin, αB crystallin, ubiquitin, moesin and annexin V. Immunization against CD63 did not change the accumulation of CD63 in the RPE/choroid. (See FIG. 8.) Furthermore, immunization against CD63 did not change the accumulation of $\beta_s$-crystallin, αB crystallin, ubiquitin or moesin in the RPE/choroid in any interpretable manner (data not shown). However, immunization against CD63 did alter the accumulation of annexin V in the RPE/choroid.

Group 3: Conclusions

The results from Group 3 demonstrate that immunization against certain antigens, for example CD63, is effective at reducing the accumulation of certain proteins on Bruch's membrane (annexin V), but not necessarily the same proteins that were affected by immunization to $\beta_s$-crystallin. However, it is possible that CD63 antibody was effective at reducing the deposition of other proteins, in addition to annexin V, which was not tested. Mice immunized with CD63 had high antibody titers. Nevertheless, the deposition of CD63 was not consistently altered.

Therefore, these results suggest that immunization against certain intracellular proteins may prevent or decrease the accumulation of drusen in human subjects. Furthermore, based on the results from Groups 1, 2 and 3, a mixture of intracellular proteins may be useful for immunotherapy to prevent or decrease the accumulation of drusen in human subjects.

All publications and patent applications cited in this specification are herein incorporated by reference as if each individual publication or patent application were specifically and individually indicated to be incorporated by reference.

We claim:

1. A method for treating drusen in a patient having macular drusen or at risk for developing macular drusen, the method comprising administering a pharmaceutical composition comprising β$_s$-crystallin to the patient in a manner effective for stimulating an antibody-mediated immune response against β$_s$-crystallin, wherein the composition comprises:
    (a) an effective amount of β$_s$-crystallin comprising the full-length amino acid sequence of SEQ ID NO:1, wherein the amount of β$_s$-crystallin is 1-80 µg and the amount is effective for stimulating an antibody-mediated immune response against β$_s$-crystallin after the composition is administered to the patient; and
    (b) a pharmaceutical carrier, excipient, or diluent.

2. The method of claim 1, wherein the vaccine is administered under a prime-boost vaccination regimen.

3. The method according to claim 1, wherein the composition further comprises a polypeptide selected from a group consisting of histone H1, histone H2A, histone H2B, histone H2AC, histone H2AZ, histone H2A/O, histone H2A2, histone H2BF, histone h2bc, histone H3, histone H4, aldehyde dehydrogenase 3, aldehyde dehydrogenase 5, ATP synthase α-chain of mitochondria, cell adhesion protein SQM1, creatine kinase B, enolase 2, aldolase A, malate dehydrogenase 1, pyruvate dehydrogenase, pyruvate kinase, recoverin, lactate dehydrogenase A, protein kinase inhibitor β, glucose phosphate isomerase, cyclophilin A, phosphoglycerate kinase, calmodulin 2, G3PDH, dystrobrevin α, phosphoinositide-3-kinase, triosephosphate isomerase 1, 14-3-3 β, apolipoprotein A1, phospholipase A2, myosin, α-B-crystallin, β-A3-crystallin, β-A4-crystallin, β-B1-crystallin, β-B2-crystallin, polyubiquitin, ubiquitin, peroxiredoxin, VEGF, retinoic acid binding protein 3, calrecticulin, calrecticulin precursor, CD63, CD81, LAMP-2, actin β, actinin α, vimentin, plectin 1, actin a2, tubulin α1a, tubulin, α3, tubulin β, and combinations thereof.

4. The method of claim 1, wherein the composition further comprises an adjuvant.

5. A method for treating drusen in a patient having macular degeneration or at risk for developing macular degeneration, the method comprising administering a pharmaceutical composition comprising β$_s$-crystallin to the patient in a manner effective for stimulating an antibody-mediated immune response against β$_s$-crystallin, wherein the composition comprises:
    (a) an effective amount of β$_s$-crystallin comprising the full-length amino acid sequence of SEQ NO:1, wherein the amount of β$_s$-crystallin is 1-80 µg and the amount is effective for stimulating an antibody-mediated immune response against β$_s$-crystallin after the composition is administered to the patient; and
    (b) a pharmaceutical carrier, excipient, or diluent.

6. The method of claim 5, wherein the vaccine is administered under a prime-boost vaccination regimen.

7. The method according to claim 5, wherein the composition further comprises a polypeptide selected from a group consisting of histone H1, histone H2A, histone H2B, histone H2AC, histone H2AZ, histone H2A/O, histone H2A2, histone H2BF, histone h2bc, histone H3, histone H4, aldehyde dehydrogenase 3, aldehyde dehydrogenase 5, ATP synthase α-chain of mitochondria, cell adhesion protein SQM1, creatine kinase B, enolase 2, aldolase A, malate dehydrogenase 1, pyruvate dehydrogenase, pyruvate kinase, recoverin, lactate dehydrogenase A, protein kinase inhibitor β, glucose phosphate isomerase, cyclophilin A, phosphoglycerate kinase, calmodulin 2, G3PDH, dystrobrevin α, phosphoinositide-3-kinase, triosephosphate isomerase 1, 14-3-3 β, apolipoprotein A1, phospholipase A2, myosin, α-B-crystallin, β-A3-crystallin, β-A4-crystallin, β-B1-crystallin, β-B2-crystallin, polyubiquitin, ubiquitin, peroxiredoxin, VEGF, retinoic acid binding protein 3, calrecticulin, calrecticulin precursor, CD63, CD81, LAMP-2, actin β, actinin α, vimentin, plectin 1, actin a2, tubulin α1a, tubulin, α3, tubulin β, and combinations thereof.

8. The method of claim 5, wherein the composition further comprises an adjuvant.

9. The method of claim 1, wherein the composition administered in the method comprises β$_s$-crystallin in an amount of 1-40 µg.

10. The method of claim 1, wherein the composition administered in the method comprises β$_s$-crystallin in an amount of 1-20 µg.

11. The method of claim 5, wherein the composition administered in the method comprises β$_s$-crystallin in an amount of 1-40 µg.

12. The method of claim 5, wherein the composition administered in the method comprises β$_s$-crystallin in an amount of 1-20 µg.

* * * * *